United States Patent [19]

Hardies et al.

[11] 4,022,609
[45] May 10, 1977

[54] HERBICIDAL FLUORINATED CARBONATES

[75] Inventors: Donald E. Hardies, Wadsworth; Jay K. Rinehart, Akron, both of Ohio

[73] Assignee: PPG Industries, Inc., Pittsburgh, Pa.

[22] Filed: Sept. 12, 1974

[21] Appl. No.: 505,419

Related U.S. Application Data

[62] Division of Ser. No. 299,968, Oct. 24, 1972, Pat. No. 3,852,464, which is a division of Ser. No. 76,275, Sept. 28, 1970, Pat. No. 3,742,010.

[52] U.S. Cl. .................................................. 71/106
[51] Int. Cl.² ........................................ A01N 9/24
[58] Field of Search ..................................... 71/106

[56] References Cited

UNITED STATES PATENTS

| | | | |
|---|---|---|---|
| 3,130,037 | 4/1964 | Scherer et al. | 71/106 |
| 3,234,260 | 2/1966 | Pianka et al. | 260/463 |
| 3,359,296 | 12/1967 | Newallis et al. | 260/455 B |
| 3,453,318 | 7/1969 | Pianka | 71/106 X |
| 3,636,037 | 1/1972 | Donninger et al. | 71/106 |

*Primary Examiner*—Glennon H. Hollrah
*Attorney, Agent, or Firm*—Robert J. Grassi; Mark Levin

[57] ABSTRACT

Fluorinated carbonates are described which are useful as miticides. These carbonates often possess herbicidal, insecticidal, and/or fungicidal properties. Examples of the fluorinated carbonates are 2',4'-dinitro-6'-sec-butylphenyl-2,2,2-trifluoroethyl carbonate; 2',4'-dinitro-6'-sec-butylphenyl-2,2,3,3-tetrafluoropropyl carbonate and 2',4'-dinitro-6'-cyclohexylphenyl 2,2,3,3-tetrafluoropropyl carbonate.

15 Claims, No Drawings

HERBICIDAL FLUORINATED CARBONATES

This is a division of application Ser. No. 299,968, filed Oct. 24, 1972, now U.S. Pat. No. 3,852,464 issued Dec. 3, 1941, which is a division of application Ser. No. 76,275 filed Sept. 28, 1970, now U.S. Pat. No. 3,742,010, issued June 26, 1973.

In accordance with this invention, there are provided carbonates which are effective as miticides and which also ofen possess herbicidal, insecticidal and/or fungicidal properties.

Carbonates here contemplated may be represented by the formula

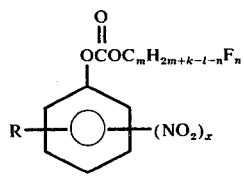

(I)

wherein
$x$ is 1, 2 or 3;
$k$ is $-2$, 0 or 2; $m$ is an integer ranging from 1 to 15 when $k$ is 2;
$m$ is an integer ranging from 2 to 15 when $k$ is 0 or $-2$;
$n$ is an integer ranging from 1 to $(2m+k-1)$; and
R is hydrogen, lower alkyl, halo lower alkyl, lower alkenyl, halo lower alkenyl, lower alkylthio, halo lower alkylthio, lower alkenylthio, halo lower alkenylthio, lower cycloalkyl or halo lower cycloalkyl.

The value for $k$ depends upon the type of bonding in the $-C_mH_{2m+k-1-n}F_n$ radical. In general, for aliphatic straight or branched chain radicals $$k = 2 - 2d - 4t$$

where
$d$ is the number of double bonds in the radical, and
$t$ is the number of triple bonds in the radical.

Thus, for aliphatic, straight, or branched chain radicals when $k = 2$ the radical is a fluoroalkyl, when $k = 0$ the radical is a fluoroalkenyl, and when $k = -2$ the radical is a fluoroalkynyl. Most often, $k = 2$.

R typically contains up to 8 carbon atoms. It ordinarily is a straight or branched lower alkyl group or halo lower alkyl group having 1 to 8 carbon atoms. Often such groups having from 1 to 4 carbon atoms are used. The secondary butyl group is preferred. When R is lower cycloalkyl or halo lower cycloalkyl, it ordinarily contains from 3 to 8 carbon atoms. Most often such groups have from 5 to 8 carbon atoms. Of these cyclic groups, cyclohexyl is preferred.

When R is halo substituted, the halo substituents are usually fluoro, chloro, bromo and/or iodo. Chloro and/or fluoro are preferred.

The value of $m$ may range from 1 to 15 or more; however, ranges from 2 to 11 or from 3 to 11 are more common. When the value of $k$ is other than 2, $m$ cannot be 1.

While the value of $n$ may range from 1 to $(2m+k-1)$, $n$ usually ranges from 3 to $(2m+k-1)$. Often $n$ is 3 or 4. The value of $n$ is also frequently an even integer ranging from 4 to 20.

The nitro groups and R may be located in any position on the ring. Often the phenyl ring is substituted by two nitro groups. While these groups may be located in any position, it is preferred that they be located in the 2',4'-positions. Although R may be located in any of the 3',5' or 6'-positions when nitro groups are in the 2',4'-positions, the preferred location for R is the 6'-position under such circumstances. When the criteria are met, a class results which may be represented by the following formula:

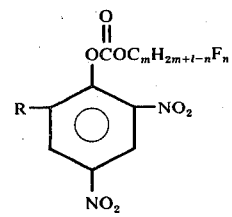

(II)

wherein
$m$ is an integer ranging from 1 to 15, more usually ranging from 2 to 11 or 3 to 11;
$n$ is an integer ranging from 1 to $(2m+1)$; and
R is lower alkyl or halo lower alkyl ordinarily containing from 1 to 8 carbon atoms or cycloalkyl or halo cycloalkyl ordinarily containing from 3 to 8 carbon atoms. When R is lower alkyl or halo lower alkyl, it usually contains from 1 to 4 carbon atoms. When R is cycloalkyl or halo cycloalkyl it usually contains from 5 to 8 carbon atoms. R is preferably secondary butyl or cyclohexyl.

An important class falling within the generic invention is represented by the formula:

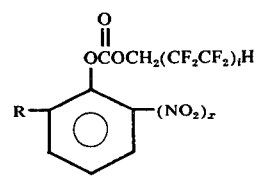

(III)

wherein
$x$ is 1, 2 or 3;
$i$ is an integer ranging from 1 to 7, more often ranging from 1 to 5; and
R is lower alkyl or halo lower alkyl ordinarily containing from 1 to 8 carbon atoms or lower cycloalkyl or halo lower cycloalkyl ordinarily containing from 3 to 8 carbon atoms. When R is lower alkyl or halo lower alkyl, it usually contains from 1 to 4 carbon atoms. When R is lower cycloalkyl or halo lower cycloalkyl, it usually contains from 5 to 8 carbon atoms. R is preferably secondary butyl or cyclohexyl.

The nitro groups and R may be located in any position on the ring. Often the ring is substituted by two nitro groups which are usually in the 2',4'-positions while R is usually located in the 6'-position. This results in the subclass:

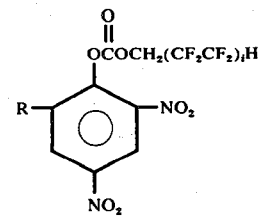

(IV)

wherein

*i* is an integer ranging from 1 to 7, more often ranging from 1 to 5; and

R is lower alkyl or halo lower alkyl ordinarily containing from 1 to 8 carbon atoms or lower cycloalkyl or halo lower cycloalkyl ordinarily containing from 3 to 8 carbon atoms. When R is lower alkyl or halo lower alkyl, it usually contains from 1 to 4 carbon atoms. When R is lower cycloalkyl or halo lower cycloalkyl, it usually contains from 5 to 8 carbon atoms. R is preferably secondary butyl or cyclohexyl.

Of especial importance are the compounds 2',4'-dinitro-6'-sec-butylphenyl 2,2,3,3-tetrafluoropropyl carbonate:

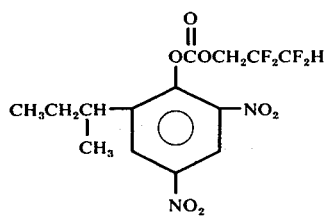
(V)

and 2',4'-dinitro-6'-cyclohexylphenyl 2,2,3,3-tetrafluoropropyl carbonate:

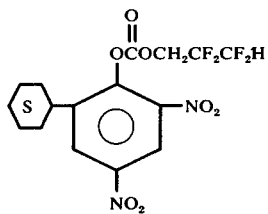
(VI)

Another important class falling within the generic invention is represented by the formula

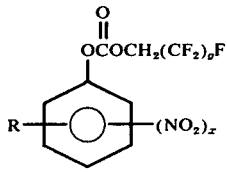
(VII)

wherein

*x* is 1, 2 or 3;

*g* is an integer ordinarily ranging from 1 to 14 and, most often, from 1 to 11 or 4 to 11; and R is lower alkyl or halo lower alkyl ordinarily containing from 1 to 8 carbon atoms or lower cycloalkyl or halo lower cycloalkyl containing from 3 to 8 carbon atoms. When R is lower alkyl or halo lower alkyl, it usually contains from 1 to 4 carbon atoms. When R is lower cycloalkyl or halo lower cycloalkyl, it usually contains from 5 to 8 carbon atoms. R is preferably secondary butyl or cyclohexyl.

The nitro groups and R may be located in any position on the ring. Often the ring is substituted by two nitro groups which are usually in the 2',4'-positions while R is usually located in the 6'-position. This results in the subclass:

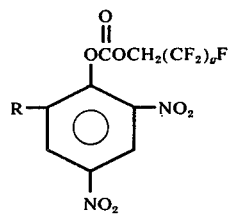
(VIII)

wherein

*g* is an integer ordinarily ranging from 1 to 14 and, most often, from 1 to 11 or 4 to 11; and R is lower alkyl or halo lower alkyl ordinarily containing from 1 to 8 carbon atoms or lower cycloalkyl or halo lower cycloalkyl ordinarily containing from 3 to 8 carbon atoms. When R is lower alkyl or halo lower alkyl, it usually contains from 1 to 4 carbon atoms. When R is lower cycloalkyl or halo lower cycloalkyl, it usually contains from 6 to 8 carbon atoms. R is preferably secondary butyl or cyclohexyl.

Of importance is the compound 2',4'-dinitro-6'-sec-butylphenyl 2,2,2-trifluoroethyl carbonate:

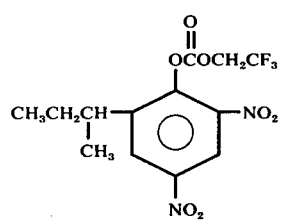
(IX)

Still another important class falling within the generic invention is represented by the formula:

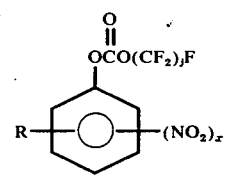
(X)

wherein

*x* is 1, 2 or 3;

*l* is an integer ranging from 1 to 15, more often ranging from 2 to 11 or 3 to 11; and R is lower alkyl or halo lower alkyl ordinarily containing from 1 to 8 carbon atoms or lower cycloalkyl or halo lower cycloalkyl ordinarily containing from 3 to 8 carbon atoms. When R is lower alkyl or halo lower alkyl, it usually contains from 1 to 4 carbon atoms. When R is lower cycloalkyl or halo lower cycloalkyl, it usually contains from 5 to 8 carbon atoms. R is preferably secondary butyl or cyclohexyl.

The nitro groups and R may be located in any position on the ring. Often the ring is substituted by two nitro groups which are usually in the 2',4'-positions while R is usually located in the 6'-position. This results in the subclass:

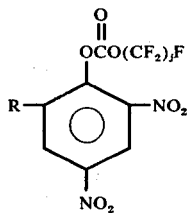

(XI)

wherein

*l* is an integer ordinarily ranging from 1 to 15, more often from 2 to 11 or 3 to 11; and R is lower alkyl or halo lower alkyl ordinarily containing from 1 to 8 carbon atoms or lower cycloalkyl or halo lower cycloalkyl ordinarily containing from 3 to 8 carbon atoms. When R is lower alkyl or halo lower alkyl, it usually contains from 1 to 4 carbon atoms. When R is lower cycloalkyl or halo lower cycloalkyl, it usually contains from 5 to 8 carbon atoms. R is preferably secondary butyl or cyclohexyl.

Compounds which exemplify the carbonates of the invention are:

2'-nitro-4'-methylphenyl fluoromethyl carbonate
2'-nitro-4'-pentylphenyl 2,2,2-trifluoroethyl carbonate
2'-nitro-5'-(1-chloromethylethyl)phenyl 2-(2,2,2-trifluoroethyl)-4,4,4-trifluorobutyl carbonate
2'-nitro-5'-(2,4-dimethylhexyl)phenyl 1H,1H,9H-hexadecafluorononyl carbonate
2'-nitro-5'-cyclooctylphenyl 1H,1H,13H-tetracosafluorotridecyl carbonate
2'-nitro-6'-sec-butylphenyl perfluoroethyl carbonate
2'-nitro-6'-trifluoromethylphenyl 8,8,8-trifluorooctyl carbonate
2'-nitro-6'-sec-butylphenyl 1H,1H,15H-octacosafluoropentadecyl carbonate
2'-nitro-6'-ethylphenyl 1,2-difluoroethyl carbonate
2'-nitrophenyl perfluoropropyl carbonate
3'-nitro-2'-ethylphenyl 2,2,2-trifluoroethyl carbonate
3'-nitro-2'-sec-butylphenyl 3,3-difluoro-2-propenyl carbonate
3'-nitro-2'-propylphenyl 1,1,3,3,6,6-hexafluorooctyl carbonate
3'-nitro-5'-vinylphenyl 3,3,4,4-tetrafluorobutyl carbonate
3'-nitro-5'-methylphenyl 1H,1H-tridecafluoroheptyl carbonate
3'-nitro-5'-isopropylphenyl 1H,1H,5H-octafluoropentyl carbonate
4'-nitro-2'-methylphenyl trifluoromethyl carbonate
4'-nitro-2'-ethylphenyl 3,3-bis(pentafluoroethyl)-1,1,-2,2,4,4,5,5,6,6-undecafluoro hexyl carbonate
4'-nitro-3'-nitro-3'-propylphenyl 2-fluoroethyl carbonate
4'-nitro-3'-ethylphenyl 12-fluorotetradecyl carbonate
4'-nitro-3'-methylphenyl perfluorovinyl carbonate
4'-nitro-3'-(2,4,6-trifluorocyclohexyl)phenyl 1H,1H,5H-octafluoropentyl carbonate
4'-nitro-3'-(3-methylheptyl)phenyl 2,2,-difluorobutyl carbonate
2',3'-dinitro-4'-methylphenyl perfluoropropyl carbonate
2',3'-dinitro-4'-(methylthio)phenyl 3,3-bis(trifluoromethyl)-4,4,4-trifluorobutyl carbonate
2',3'-dinitro-5'-sec-butylphenyl perfluoropentadecyl carbonate
2',3'-dinitro-5'-(methylthio)phenyl 3-fluorobutyl carbonate
2',3'-dinitro-5'-isopropylphenyl 1H,1H,7H-dodecafluoroheptyl carbonate
2',3'-dinitro-5'-heptylphenyl 2,3-difluoropentyl carbonate
2',3'-dinitro-5'-methylphenyl fluoromethyl carbonate
2',3'-dinitro-6'-sec-butylphenyl 1,2,2-trifluoroethyl carbonate
2',4'-dinitrophenyl 2,2,3,3-tetrafluoropropyl carbonate
2',4'-dinitro-6'-sec-butylphenyl 2,2,3,3-tetrafluoropropyl carbonate
2',4'-dinitro-6'-methylphenyl perfluoro-4-octynyl carbonate
2',4'-dinitro-3'-methylphenyl 3-fluoropropyl carbonate
2',4'-dinitro-3'-(2-chloroethyl)phenyl 4,7-difluoroheptyl carbonate
2',4'-dinitro-3'-butylphenyl 1,1,4,4,8,10-hexafluoro-6-(1,2,2-trifluoroethyl)undecyl carbonate
2',4'-dinitro-3'-pentafluorocyclohexylphenyl 2,2,3,3-tetrafluoropropyl carbonate
2',4'-dinitro-5'-allylphenyl 1,3-difluoropropyl carbonate
2',4'-dinitro-5'-(2-fluoroethyl)phenyl 1-fluoropropyl carbonate
2',4'-dinitro-5'-isopropylphenyl 2,2,2-trifluoroethyl carbonate
2',4'-dinitro-5'-ethylphenyl 1-(fluoromethyl)-2-fluoroethyl carbonate
2',4'-dinitro-6'-methylphenyl 2,2,2-trifluoroethyl carbonate
2',4'-dinitro-6'-methylphenyl 2,2,3,3-tetrafluoropropyl carbonate
2',4'-dinitrophenyl 1H,1H,9H-hexadecafluorononyl carbonate
2',4'-dinitro-6'-pentylphenyl 1H,1H,9H-hexadecafluorononyl carbonate
2',4'-dinitro-6'-ethylphenyl 2,2,2-trifluoroethyl carbonate
2',4'-dinitro-6'-ethylphenyl 4-fluoro-2-butynyl carbonate
2',4'-dinitro-6'-isopropylphenyl 2,2,3,3-tetrafluoropropyl carbonate
2',4'-dinitro-6'-ethylphenyl perfluorodecyl carbonate
2',4'-dinitro-6'-isobutylphenyl 2,2-difluorobutyl carbonate
2',4'-dinitro-6'-isobutylphenyl 2,2,3,3-tetrafluoropropyl carbonate
2',4'-dinitro-6'-sec-butylphenyl 1-(trifluoromethyl)-2,2,2-trifluoroethyl carbonate
2',4'-dinitor-6'-sec-butylphenyl 2,2,4,4,6,6,8,8,9,9-decafluoro-8-nonenyl carbonate
2',4'-dinitro-6'-sec-butylphenyl fluoromethyl carbonate
2',4'-dinitro-6'-sec-butylphenyl difluoromethyl carbonate
2',4'-dinitro-6'-sec-butylphenyl trifluoromethyl carbonate
2',4'-dinitro-6'-sec-butylphenyl 2-fluoroethyl carbonate
2',4'-dinitro-6'-sec-butylphenyl 2,2-difluoroethyl carbonate
2',4'-dinitro-6'-sec-butylphenyl 2,2,2-trifluoroethyl carbonate
2',4'-dinitro-6'-sec-butylphenyl 2,2,3,3-tetrafluoropropyl carbonate 2',4'-dinitro-6'-sec-butylphenyl 1H,1H,5H-octafluoropentyl carbonate
2',4'-dinitro-6'-sec-butylphenyl 1H,1H,7H-dodecafluoroheptyl carbonate
2',4'-dinitro-6'-sec-butylphenyl 1H,1H,9H-hexadecafluorononyl carbonate
2',4'-dinitro-6'-sec-butylphenyl 1H,1H,11H-eicosafluoroundecyl carbonate
2',4'-dinitro-6'-sec-butylphenyl 1H,1H,13H-tetracosafluorotridecyl carbonate
2',4'-dinitro-6'-sec-butylphenyl 1H,1H,15H-octacosafluoropentadecyl carbonate
2',4'-dinitro-6'-sec-butylphenyl perfluoropentadecyl carbonate
2',4'-dinitro-6'-sec-butylphenyl 1H,1H,4H-docasafluorododecyl carbonate
2',4'-dinitro-6'-sec-butylphenyl 2,2,3,3,3-pentafluoropropyl carbonate
2',4'-dinitro-6'-sec-butylphenyl 1H,1H-nonafluoropentyl carbonate
2',4'-dinitro-6'-sec-butylphenyl 1H,1H-undecafluorohexyl carbonate
2',4'-dinitro-6'-sec-butylphenyl 1H,1H-tridecafluoroheptyl carbonate
2',4'-dinitro-6'-sec-butylphenyl 1H,1H-pentadecafluorooctyl carbonate
2',4'-dinitro-6'-sec-butylphenyl 1H,1H-heptadecafluorononyl carbonate
2',4'-dinitro-6'-sec-butylphenyl 1H,1H-nonadecafluorodecyl carbonate
2',4'-dinitro-6'-sec-butylphenyl 1H,1H-heneicosafluoroundecyl carbonate
2',4'-dinitro-6'-sec-butylphenyl 1H,1H-tricosafluorododecyl carbonate
2',4'-dinitro-6'-sec-butylphenyl 1H,1H-pentacosafluorotridecyl carbonate
2',4'-dinitro-6'-sec-butylphenyl 1H,1H,-heptacosafluorotetradecyl carbonate
2',4'-dinitro-6'-sec-butylphenyl 1H,1H-nonacosafluoropentadecyl carbonate
2',4'-dinitro-6'-sec-butylphenyl trifluoromethyl carbonate
2',4'-dinitro-6'-sec-butylphenyl perfluoroethyl carbonate
2',4'-dinitro-6'-sec-butylphenyl perfluoropropyl carbonate
2',4'-dinitro-6'-sec-butylphenyl perfluorobutyl carbonate
2',4'-dinitro-6'-sec-butylphenyl perfluoropentyl carbonate
2',4'-dinitro-6'-sec-butylphenyl perfluorohexyl carbonate
2',4'-dinitro-6'-sec-butylphenyl perfluoroheptyl carbonate
2',4'-dinitro-6'-sec-butylphenyl perfluorooctyl carbonate
2',4'-dinitro-6'-sec-butylphenyl perfluorononyl carbonate
2',4'-dinitro-6'-sec-butylphenyl perfluorodecyl carbonate
2',4'-dinitro-6'-sec-butylphenyl perfluoroundecyl carbonate
2',4'-dinitro-6'-sec-butylphenyl perfluorododecyl carbonate
2',4'-dinitro-6'-sec-butylphenyl perfluorotridecyl carbonate
2',4'-dinitro-6'-sec-butylphenyl perfluorotetradecyl carbonate
2',4'-dinitro-6'-sec-butyphenyl perfluoropentadecyl carbonate
2',4'-dinitro-6'-sec-butylphenyl 3,3-bis(trifluoromethyl)-1,1,2,2,4,4,5,5,5-nonafluoropentyl carbonate
2',4'-dinitro-6'-sec-butylphenyl 1,1,2,2,3,3,4,4-octakis(trifluoromethyl)-5,5,5-trifluoropentyl carbonate
2',4'-dinitro-6'-sec-butylphenyl 3-(pentafluoroethyl)-2,2,4,4-tetrakis(trifluoromethyl)-2,2,5,5,5-pentafluoropentyl carbonate
2',4'-dinitro-6'-sec-butylphenyl 3,5,7-tris(trifluoromethyl)-1,1,2,2,3,4,4,5,6,6,7,8,8,8-tetradecafluorooctyl carbonate
2',4'-dinitro-6'-sec-butylphenyl 1-trifluoromethyl-2,2,2-trifluoroethyl carbonate
2',4'-dinitro-6'-tert-butylphenyl 2,2,3,3-tetrafluoropropyl carbonate
2',4'-dinitro-6'-cyclopropylphenyl 2,2,2-trifluoroethyl carbonate
2',4'-dinitro-6'-cyclobutylphenyl 2,2,2-trifluoroethyl carbonate
2',4'-dinitro-6'-cyclopentylphenyl 2,2,2-trifluoroethyl carbonate
2',4'-dinitro-6'-cyclohexylphenyl 2,2,2-trifluoroethyl carbonate
2',4'-dinitro-6'-cycloheptylphenyl 2,2,2-trifluoroethyl carbonate
2',4'-dinitro-6'-cyclooctylphenyl 2,2,2-trifluoroethyl carbonate
2',4'-dinitro-6'-cyclopropylphenyl 2,2,3,3-tetrafluoropropyl carbonate
2',4'-dinitro-6'-cyclobutylphenyl 2,2,3,3-tetrafluoropropyl carbonate
2',4'-dinitro-6'-cyclopentylphenyl 2,2,3,3-tetrafluoropropyl carbonate
2',4'-dinitro-6'-cyclohexylphenyl 1-(trifluoromethyl)-2,2,2-trifluoroethyl carbonate
2',4'-dinitro-6'-cyclohexylphenyl 2,2,3,3-tetrafluoropropyl carbonate
2',4'-dinitro-6'-cyclohexylphenyl 1H,1H,5H-octafluoropentyl carbonate
2',4'-dinitro-6'-cyclohexylphenyl 1H,1H,7H-dodecafluoroheptyl carbonate
2',4'-dinitro-6'-cyclohexylphenyl 1H,1H,9H-hexadecafluorononyl carbonate
2',4'-dinitro-6'-cyclohexylphenyl 1H,1H,11H-eicosafluoroundecyl carbonate
2',4'-dinitro-6'-cyclohexylphenyl 1H,1H,13H-tetracosafluorotridecyl carbonate
2',4'-dinitro-6'-cyclohexylphenyl 1H,1H,15H-octacosafluoropentadecyl carbonate
2',4'-dinitro-6'-cycloheptylphenyl 2,2,3,3-tetrafluoropropyl carbonate
2',4'-dinitro-6'-cyclooctylphenyl 2,2,3,3-tetrafluoropropyl carbonate
2',4'-dinitro-6'-(4-fluorocycloheptyl)phenyl 2,2,3,3-tetrafluoropropyl carbonate
2',4'-dinitro-6'-ethylphenyl 1H,1H,13H-tetracosafluorotridecyl carbonate
2',4'-dinitro-6'-(methylthio)phenyl 1H,1H,13H-docosafluoro-9-tridecenyl carbonate
2',4'-dinitro-6'-allylphenyl 2,2,4,4-tetrafluorohexyl carbonate
2',4'-dinitro-6'-octylphenyl 1H-pentafluoropropyl carbonate
2',4'-dinitro-6'-sec-butylphenyl 1H-pentafluoropropyl carbonate
2',4'-dinitro-6'-sec-butylphenyl perfluoropropyl 2',4'-dinitro-6'-pentylphenyl 1,1-bis(trifluoroethyl)-2,2,2-trifluoroethyl carbonate
2',4'-dinitro-6'-propylphenyl 2,2-bis(trifluoromethyl)-3,3,3-triifuloropropyl carbonate
2',4'-dinitro-6'-methylphenyl 4-fluoropentyl carbonate
2',4'-dinitro-6'-sec-butylphenyl 2-(2-fluoroethyl)-3-[1-(difluoromethyl)-3,3-(difluoro)butyl]-4,7,7-trifluoro-5-methylheptyl carbonate
2',4'-dinitro-6'-(vinylthio)phenyl perfluorobutyl carbonate
2',4'-dinitro-6'-(4-butenyl)phenyl 2,2-difluoroethyl carbonate
2',4'-dinitro-(4,4-difluoro-4-butenyl)phenyl 3,3,3-trifluoropropyl carbonate
2',4'-dinitro-6'-ethylphenyl 1-trifluoromethyl 2,2-difluoroethyl-3-(1,1,2,2-tetrafluoroethyl-1,3,4,4,5,5,5-heptafluoropentyl carbonate
2',4'-dinitro-6'-neopentylphenyl 1H,1H,9H-hexadecafluoronoyl carbonate
2',4'-dinitro-6'-butylphenyl fluoromethyl carbonate
2',5'-dinitro-3'-methylphenyl trifluoromethyl carbonate
2',5'-dinitro-3'-sec-butylphenyl 1H,1H,7H-dodecafluoroheptyl carbonate
2',5'-dinitro-4'-heptylphenyl 1H,1H,7H-dodecafluoroheptyl carbonate
2',5'-dinitro-4'-(4-chlorocyclohexyl)phenyl 1H,1H,7H-dodecafluoroheptyl carbonate
2',5'-dinitro-4'-(fluoromethylthio)phenyl 2,2-difluoroethy carbonate
2',5'-dinitro-6'-dinitro-6'-(trifluoromethyl)phenyl trifluoromethyl carbonate
2',5'-dinitro-6'-[1-(trifluoromethyl)-2,2,2-(trifluoro)ethylthio]phenyl perfluoro-10-tetradecnyl carbonate
2',5'-dinitro-6'-isopropylphenyl perfluoroethyl carbonate 2',6'-dinitrophenyl 2,2,3,3-tetrafluoropropyl carbonate
2',6'-dinitro-3'-isohexylphenyl 1H,1H,9H-hexadecafluorononyl carbonate
2',6'-dinitro-3'-ethylphenyl 1H,1H,-heneicosafluoroundecyl carbonate
2',6'-dinitro-3'-propylphenyl 2-fluoropropyl carbonate
2',6'-dinitro-4'-(methylthio)phenyl 2,2,3,3-tetrafluoropropyl carbonate
2',6'-dinitro-4'-tert-butylphenyl 3,5,7,10,12,14-hexafluoro-8-pentadecynyl carbonate
2',6'-dinitro-4'-isopropylphenyl 1,2-difluoroethyl carbonate
2',6'-dinitro-4'-isobutylphenyl perfluoropropyl carbonate
3',4'-dinitro-2'-methylphenyl 1H,1H,7H-dodecylfluoroheptyl carbonate
3',4'-dinitro-2'-(chloromethyl)phenyl 1,1,3,3,5,5-hexafluoropentyl carbonate
3',4'-dinitro-5'-methylphenyl 2,2,3,3-tetrafluoropropyl carbonate
3',4'-dinitro-5'-ethylphenyl 1,1,2,2,4,4,5,5,5-nonafluoro-3,3-bis(pentafluoroethyl)pentyl carbonate
3',4'-dinitro-5'-butylphenyl perfluorohexyl carbonate
3',4'-dinitro-5'-sec-butylphenyl 1H,1H,5H-octafluoropentyl carbonate
3',4'-dinitro-6'-isopropylphenyl 1H,1H,13H-tetracosafluorotridecyl carbonate
3',4'-dinitro-6'-(2,4,6,8-tetrafluorocyclooctyl)phenyl 2,2,3,3-tetrafluoropropyl carbonate
3',4'dinitro-6'-methylphenyl 1H,1H13H-tetracosafluorotridecyl carbonate
3',4'-dinitro-6'-isopropylphenyl 1,1,2-tris(trifluoromethyl)-2,3,3,3-tetrafluoropropyl carbonate
3',4'-dinitro-6'-sec-butylphenyl difluoromethyl carbonate
3',5'-dinitrophenyl 1,2-difluoroethyl carbonate 3',5'-dinitro-2'-(fluoromethyl)phenyl 1H,1H,5H-octafluoropentyl carbonate
3',5'-dinitro-2'-(bromoethyl)phenyl 1H,1H,5H-octafluoropentyl carbonate
3',5'-dinitro-4'-methhylphenyl perfluoroheptyl carbonate
3',5'-dinitro-4'-(methylthio)phenyl trifluoromethyl carbonate
3',5'-dinitro-4'-isopropylphenyl difluromethyl carbonate
2',3',4'-trinitro-5'-methylphenyl 1H,1H,5H-octafluoropentyl carbonate
2',3',4'-trinitro-5'-ethylphenyl 1,2-difluoroethyl carbonate
2',3',4'-trinitro-6'-methylphenyl 1H,1H,15H-octacosafluoropentadecyl carbonate
2',3',4'-trinitro-6'-methylphenyl 2,2,2-trifluoroethyl carbonate
2',3',5'-trinitro-4'-methylphenyl 1H,1H,6H,12H-heneicosafluorododecyl carbonate
2',3',5'-trinitro-4'-pentachlorocyclopropylphenyl trifluoromethyl carbonate
2',3',5'-trinitro-4'-propylphenyl 3,3,4-trifluorobutyl carbonate
3',3',5'-trinitro-4'-trifluoromethylphenyl 1H,1H,-undecafluoroheyl carbonate
2',3',5'-triinitro-6'-methylphenyl fluoromethyl carbonate
2',3',6'-trinitro-4'-isopropylphenyl 1H,1H,11H-eicosafluoroundecyl carbonate
2',3',6'-trinitro-4'-(4,4,4-trifluoro-2-butenylthio)phenyl trifluoromethyl carbonate
2',3',6'-trinitro-4'-(ethylthio)phenyl 1,2,3-trifluoropropyl carbonate
2',3',6'-trinitro-5'-isopropylphenyl 1H,2H,13H-tetracosafluorotridecyl carbonate
2',3',6'-trinitro-5'-isopropylphenyl 1H,1H,13-H-tetracosafluorotridecyl carbonate
2',3',6'-trinitro-5'methylphenyl 1,2-difluoroethyl carbonate
2',4',5'-trinitro-3'-methylphenyl perfluoroethyl carbonate
2',4',5'-trinitrophenyl 2,2,2-trifluoroethyl carbonate
2',4',5'-trinitro-6'-sec-butylphenyl trifluoromethyl carbonate
2',4',5'-trinitro-6'-isopropylphenyl 1,2,3,4,5,6-hexafluorohexyl carbonate
2',4',5'-trinitro-6'-methylphenyl 2-fluoroethyl carbonate
2',4',6'-trinitro-3'-ethylphenyl 2fluoropropyl carbonate
2',4',6'-trinitro-3'-methylphenyl 1H,1H,9H-hexadecafluorononyl carbonate
2',4',6'-trinitro-3'-methylphenyl perfluoroheptyl carbonate
3',4',5'-trinitro-2'-methylphenyl 2,2,3,3-tetrafluoropropyl carbonate
3',4',5 -trinitro-2'-sec-butylphenyl 1,2-difluoroethyl carbonate
3',4',5'-trinitro-2'-isopropylphenyl 1H,1H,11H-eicosafluoroundecyl carbonate These carbonates may be prepared by the reaction of a chloroformate with a substituted phenol. The reaction may conveniently be conducted in a solvent.

Each of Examples I – XV illustrates a manner in which the contemplated carbonates may be prepared.

EXAMPLE I

Phosgene (74 g.) was condensed into anhydrous diethyl ether (200 ml.) contained in a one liter, three-necked flask at ice bath temperature. The compound 2,2,2-trifluoroethanol (25.0 g.) in diethyl ether (75 ml.) was added in a stream to the reaction mixture. Anhydrous pyridine (22 g.) in diethyl ether (25 ml.) was added dropwise to the stirred reaction mixture while maintaining a temperature of 4° to 12° C. The dropwise addition of the pyridine was accomplished over a 30-minute period. There was an instantaneous precipitation of pyridine hydrochloride upon addition of the first drop of pyridine. The reaction mixture was stirred for 3 hours while warming to room temperature. The excess phosgene was removed from the reaction mixture under a fine stream of argon. The precipitated pyridine hydrochloride was then removed by filtration and the filtrate distilled under a nitrogen bleed to remove the solvent. Distillation of the residue under a pressure of 165 Torr gave the product (17.8 g.) as a colorless liquid. the boiling point of the product was 40° C. at 165 Torr. The structure 2,2,2-trifluoroethyl chloroformate was confirmed by nuclear magnetic resonance (NMR) spectroscopy.

The sodium salt of 2,4-dinitro-6-sec-butyl phenol was prepared by combining 2,4-dinitro-6-sec-butyl phenol (7.9 g.), sodium hydroxide (2.0 g.) and water (150ml.). Unstabilized methylene chloride (100 ml.) and triethylamine (1 ml.) were then added. The compound 2,2,2-trifluoroethyl chloroformate (4.9 g.) was added dropwise to the vigorously stirred reaction mixture over a 30-minute period while maintaining the temperature in the range of 24°–27° C. The reaction mixture was stirred for an additional 15 minutes. The two layers were separated and the aqueous layer was washed with methylene chloride (100 ml.). The resulting layers were separated and the organic layer was combined with the organic layer from the first separation. The combined organic layers were washed with two portions (100 ml. each) of 10% aqueous sodium hydroxide, one portion (100 ml.) off 10% hydrochloric acid and dried over sodium sulfate. The solvent was removed on a rotary evaporator to give 5.4 g. of crude oil which crystallized upon standing. The product was recrystallized from diethyl ether--normal pentane to give 4.2 g. of yellow crystals having a melting point of 91°–93° C. The infrared spectrum showed the carbonate ester absorption at 1782 cm$^{-1}$. This product was analyzed for carbon, hydrogen and nitrogen. The results expressed in per cent by weight are shown in Table 1.

Table 1

| Analysis of 2',4'-dinitro-6'-sec-butylphenyl 2,2,2-trifluoroethyl carbonate | | | |
|---|---|---|---|
| | C | H | N |
| Calculated for $C_{13}H_{13}F_3N_2O_7$ | 42.63 | 3.58 | 7.65 |
| First Analysis | 43.32 | 3.27 | 8.04 |
| Second Analysis | 43.28 | 3.26 | 8.11 |

The product may be depicted as having the structural formula:

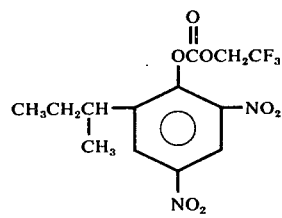

EXAMPLE II

Phosgene (74 g.) was condensed into anhydrous diethyl ether (200 ml.) contained in a one liter, three-necked flask at ice bath temperature. The compound 2,2,3,3-tetrafluoro-1-propanol (33.0 g.) in diethyl ether (75 ml.) was added in a stream to the reaction mixture. Anhydrous pyridine (22 g.) in diethyl ether (25 ml.) was added dropwise to the stirred reaction mixture while maintaining a temperature of 2° to 8° C. The dropwise addition of the pyridine was accomplished over a 20-minute period. There was an instantaneous precipitation of pyridine hydrochloride upon addition of he first drop of pyridine. The reaction mixture was stirred for 3 hours while warming to room temperature. the excess phosgene was removed from the reaction mixture under a fine stream of argon. The precipitated pyridine hydrochloride was then removed by filtration and the filtrate distilled under a nitrogen bleed to remove the solvent. distillation of the residue under a pressure of 50 Torr gave the product (33.1 g.) as a colorless liquid. The boiling point of the product was 48°–49° C. at 50 Torr. The structure 2,2,3,3,-tetrafluoropropyl chloroformate was confirmed by NMR spectroscopy.

The sodium salt of 2,4-dinitro-6-sec butyl phenol was prepared by combining 2,4-dinitro-6-sec butyl phenol (9.6 g.), sodium hydroxide (2.4 g.) and water (150 ml.). Unstabilized methylene chloride (100 ml.) and triethylamine (1 ml.) were then added. The compound 2,2,3,3-tetrafluoropropyl chloroformate (7.8 g.) was added dropwise to the vigorously stirred reaction mixture over a 15-minute period while maintaining the temperature in the range of 25°–29° C. The reaction mixture was stirred for an additional 15 minutes. The two layers were separated and the aqueous layer was washed with methylene chloride (100 m..). The resulting layers were separated and the organic layer was combined with the organic layer from the first separation. The combined organic layers were washed with two portions (100 ml. each) of 10% aqueous sodium hydroxide, one portion (100 ml.) of 10% hydrochloric acid and dried over sodium sulfate.. The solvent was removed on a rotary evaporator to give 12.0 g. of crude oil which crystallized upon cooling in ice. The product was recrystallized from diethyl ether--normal pentane to give 6.7 g. of yellow crystals having a melting point of 45°–48° C. The infrared spectrum showed the carbonate ester absorption at 1784 cm$^{-1}$. This product was analyzed for carbon, hydrogen and nitrogen. The results expressed in per cent by weight are shown in Table 2.

Table 2

Analysis of 2',4'-dinitro-6'-sec-butylphenyl 2,2,3,3-tetrafluoropropyl carbonate

|  | C | H | N |
|---|---|---|---|
| Calculated for C₁₄H₁₄F₄N₂O₇ | 42.22 | 3.54 | 7.04 |
| First Analysis | 41.96 | 3.18 | 6.96 |
| Second Analysis | 42.11 | 3.29 | — |

The produce may be depicted as having the structural formula:

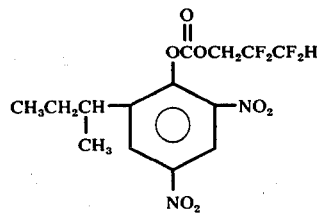

EXAMPLE III

The sodium salt of 2,4-dinitro-6-cyclohexyl phenol was prepared by combining 2,4-dinitro-6-cyclohexyl phenol (5.3 g.), sodium hydroxide (1.2 g.) and water (150 ml.). Unstabilized methylene chloride (100 ml.) and triethylamine (1 ml.) were then added. The compound 2,2,3,3-tetrafluoropropyl chloroformate (3.9 g.) was added dropwise to the vigorously stirred reaction mixture over a 10-minute period while maintaining the temperature in the range of 24°-26° C. The reaction mixture was stirred for an additional 15 minutes. The two layers were separated and the aqueous layer was washed with methylene chloride (100 ml.). The resulting layers were separated and the organic layer was combined with the organic layer from the first separation. The combined organic layers were washed with two portions (100 ml. each) of 10% aqeuous sodium hydroxide, one portion (100 ml.) of 10% hydrochloric acid, and dried over sodium sulfate. The solvent was removed on a rotary evaporator to give 5.0 g. of crude oil which crystallized upon cooling in ice. The product was recrystallized from diethyl ether —normal pentane to give 3.5 g. of pale yellow crystals having a melting point of 89°-92° C. The infrared spectrum showed the carbonate ester absorption at 1780 cm⁻¹. This product was analyzed for carbon, hydrogen and nitrogen. The results expressed in percent by weight are shown in Table 3.

Table 3

Analysis of 2',4'-dinitro-6'-cyclohexylphenyl 2,2,3,3-tetrafluoropropyl carbonate

|  | C | H | N |
|---|---|---|---|
| Calculated for C₁₆H₁₆F₄N₂O₇ | 45.29 | 3.80 | 6.60 |
| First Analysis | 44.99 | 4.03 | 6.45 |
| Second Analysis | 45.23 | 3.88 | — |

The product may be depicted as having the structural formula:

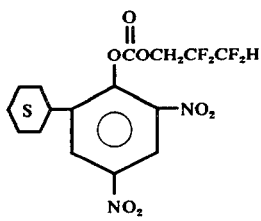

EXAMPLE IV

The sodium salt of 2,4-dinitro-6-methyl phenol was prepared by combining 2,4-dinitro-6-methyl phenol (4.5 g.), sodium hydroxide (1.3 g.) and water (150 ml.). Unstabilized methylene chloride (100 ml.) and triethylamine (1 ml.) were then added. The compound 2,2,3,3-tetrafluoropropyl chloroformate (4.4 g.) was added dropwise to the vigorously stirred reaction mixture over a 25-minute period while maintaining the temperature in the range of 22°-25° C. The reaction mixture was stirred for an additional 15 minutes. The two layers were separated and the aqueous layer was washed with methylene chloride (100 ml.). The resulting layers were separated and the organic layer was combined with the organic layer from the first separation. The combined organic layers were washed with two portions (100 ml. each) of 10% aqueous sodium hydroxide, one portion (100 ml.) of 10% hydrochloric acid, and dried over sodium sulfate. The solvent was removed on a rotary evaporator to give 5.4 g. of oil which would not crystallize. The infrared spectrum showed the carbonate ester absorption at 1783 cm⁻¹. Purity was established as about 85% by NMR spectroscopy.

The product may be depicted as having the structural formula:

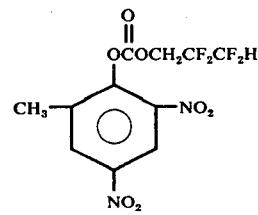

EXAMPLE V

Phosgene (148.4 g.) was condensed into anhydrous diethyl ether (200 ml.) contained in a one liter, four-necked, round-bottom flask equipped with a dropping funnel, a solid carbon dioxide condenser, a polytetrafluoroethylene blade paddle stirrer, a thermometer, and a phosgene inlet. The compound 1H,1H,7H-dodecafluoro-1-heptanol (166.1 g.) dissolved in an equal volume of diethyl ether was added in a stream to the mixture. Anhydrous pyridine (43.5 g.) dissolved in an equal volume of diethyl ether was added dropwise to the stirred reaction mixture while maintaining a temperature of 0° to 10° C. The dropwise addition of the pyridine was accomplished over a period of about one hour. The reaction mixture was stirred an additional one hour at 0° to 10° C., then for two hours while gradually warming up to room temperature. The excess phosgene was removed from the reaction mixture under a fine stream of nitrogen. The precipitated pyridine hydrochloride was then removed by filtration and washed with diethyl ether. The diethyl ether wash was squeezed out of the paper into the filtrate. The filtrate was dried with sodium sulfate and diethyl ether solvent was removed by a one-plate distillation at atmospheric pressure. One-plate distillation of the residue under reduced pressure gave produce (180.5 g.) having an assay of 94.9 per cent. The boiling point of the product, 1H,1H,7H-dodecafluoroheptyl chloroformate, was 42.0° C. at 1.1 Torr. The sodium salt of 2,4-dinitro-6-sec-butyl phenol was prepared by combining 2,4-dinitro-6-sec-butyl phenol (7.4 g.), sodium hydroxide (1.8 g.), and water (150 ml.). Unstabilized methylene chloride (100 ml.) and triethylamine (1 ml.) were then added. The compound 1H,1H,7H-dodecafluoroheptyl chloroformate (13.0 g.) was added dropwise to the vigorously stirred reaction mixture over a 45-minute period while maintaining the temperature in the range of 22°–25° C. The reaction mixture was stirred for an additional 15 minutes. The two layers were separated and the aqueous layer was washed with methylene chloride (100 ml.). The resulting layers were separated and the organic layer was combined with the organic layer from the first separation. The combined organic layers were washed with two portions (100 ml. each) of 10% aqueous sodium hydroxide, one portion (100 ml.) of 10% hydrochloric acid, and dried over sodium sulfate. The solvent was removed on a rotary evaporator to give 15.5 g. of oil which would not immediately crystallize. The infrared spectrum showed the carbonate ester absorption at 1780 cm$^{-1}$. Purity was established to be about 94 per cent by NMR spectroscopy. The product was analyzed for carbon, hydrogen and nitrogen. The results expressed in per cent by weight are shown in Table 4.

Table 4

| Analysis of 2',4'-dinitro-6'-sec-butyl 1H,1H,7H-dodecafluoroheptyl carbonate | | | |
|---|---|---|---|
| | C | H | N |
| Calculated for | | | |
| $C_{18}H_{14}F_{12}N_2O_7$ | 36.13 | 2.36 | 4.68 |
| First Analysis | 33.84 | 2.31 | 6.58 |
| Second Analysis | 34.19 | 2.14 | 6.58 |

After prolonged standing, the oil crystallized. an analytical sample was prepared by recrystallizing a 5.0 g. portion from diethyl ether—normal pentane to yield 3.1 g. of crystals having a melting point range of 55.5° to 57.5° C. The product was analyzed for carbon, hydrogen and nitrogen. The results expressed in per cent by weight are shown in Table 5.

Table 5

| Analysis of 2',4'-dinitro-6'-sec-butylphenyl 1H,1H,7H-dodecafluoroheptyl carbonate | | | |
|---|---|---|---|
| | C | H | N |
| First Analysis | 35.30 | 2.46 | 4.90 |
| Second Analysis | 35.15 | 2.41 | — |

The product may be depicted as having the structural formula:

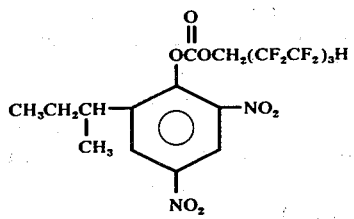

EXAMPLE VI

Phosgene (89.0 g.) was condensed into anhydrous diethyl ether (200 ml.) contained in a one liter, four-necked, round-bottom flask equipped with a dropping funnel, a solid carbon dioxide condenser, a polytetrafluoroethylene blade paddle stirrer, a thermometer, and a phosgene inlet. The compound 1H,1H,11H-eicosafluoro-1-undecanol (159.6 g.) dissolved in an equal volume of diethyl ether was added in a stream to the mixture. Anhydrous pyridine (26.1 g.) dissolved in an equal volume of diethyl ether was added dropwise to the stirred reaction mixture while maintaining a temperature of 0° – 10° C. The dropwise addition of the pyridine was accomplished over a period of about one hour. The reaction mixture was stirred an additional hour at 0°–10° C., then for two hours while gradually warming up to room temperature. The excess phosgene was removed from the reaction mixture under a fine stream of nitrogen. The precipitated pyridine hydrochloride was then removed by filtration and washed with diethyl ether. The diethyl ether wash was squeezed out of the paper into the filtrate. The filtrate was dried with sodium sulfate and diethyl ether solvent was removed by a one-plate distillation at atmospheric pressure. The solid residue was recrystallized from n-hexane, yielding crystals (89.7 g.) having an assay of 78.4 per cent and a melting point of 57.5°–58.0° C. The product was 1H,1H,11H-eicosafluoroundecyl chloroformate.

The sodium salt of 2,4-dinitro-6-sec-butyl phenol was prepared by combining 2,4-dinitro-6-sec-butyl phenol (4.8 g.), sodium hydroxide (1.2 g.), and water (150 ml.). Unstablized methylene chloride (100 ml.) and triethylamine (1 ml.) were then added. The compound 1H,1H,11H-eicosafluoroundecyl chloroformate (13.1 g.) was added dropwise to the vigorously stirred reaction mixture over a 35-minute period while maintaining the temperature in the range of 24°–26° C. The reaction mixture was stirred for an additional 15 minutes. The two layers were separated and the aqueous layer was washed with methylene chloride (100 ml.). The resulting layers were separated and the organic layer was combined with the organic layer were washed with two portions (100 ml. each) of 10% aqueous sodium hydroxide, one portion (100 ml.) of 10% hydrochloric acid, and dried over sodium sulfate. The solvent was removed on a rotary evaporator to give 14.1 g. of crude oil which crystallized. The product was recrystallized from diethyl ether—normal pentane to give 6.5 g. of crystals having a melting point of 100.5–103° C. The infrared spectrum showed the carbonate ester absorption at 1784 cm$^{-1}$. This product was analyzed for carbon, hydrogen and nitrogen. The results expressed in per cent by weight are shown in Table 6.

Table 6

| Analysis of 2',4'-dinitro-6'-sec-butylphenyl 1H,1H,11H-eicosafluoroundecyl carbonate | | | |
|---|---|---|---|
| | C | H | N |
| Calculated for | | | |
| $C_{22}H_{14}F_{20}N_2O_7$ | 33.1 | 1.77 | 3.51 |
| First Analysis | 32.56 | 1.94 | 3.65 |
| Second Analysis | 32.61 | 1.90 | — |
| Third Analysis | 32.41 | 1.97 | — |

The product may be depicted as having the structural formula:

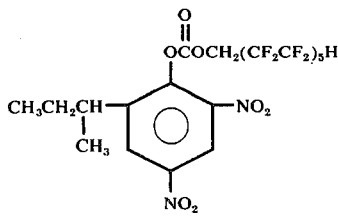

EXAMPLE VII

Phosgene (158.3 g.) was condensed into anhydrous diethyl ether (200 ml.) contained in a one liter, four-necked, round-bottom flask equipped with a dropping funnel, a solid carbon dioxide condenser, a polytetrafluoroethylene blade paddle stirrer, a thermometer, and a phosgene inlet. The compound 1-(trifluoromethyl)-2,2,2-trifluoroethanol (117.6 g.) dissolved in an equal volume of diethyl ether was added in a stream to the mixture. Anhydrous pyridine (69.6 g.) dissolved in an equal volume of diethyl ether was added dropwise to the stirred reaction mixture while maintaining a temperature of 0° to 10° C.

The dropwise addition of the pyridine was accomplished over a period of about one hour. The reaction mixture was stirred an additional hour at 0° to 10° C., then for two hours while gradually warming up to room temperature. The excess phosgene was removed from the reaction mixture. The precipitated pyridine hydrochloride was then removed by filtration and washed with diethyl ether. The diethyl ether wash was squeezed out of the paper into the filtrate. The filtrate was dried with sodium sulfate and diethyl ether solvent was removed by a one-plate distillation at atmospheric pressure. Ten-plate distillation of the residue at atmospheric pressure gave product (46.4 g.) having an assay of 93 percent. The product was 1-(trifluoromethyl)-2,2,2-trifluoroethyl chloroformate.

The sodium salt of 2,4-dinitro-6-sec-butyl phenol was prepared by combining 2,4-dinitro-6-sec-butyl phenol (8.4 g.), sodium hydroxide (2.1 g.), and water (150 ml.). Unstabilized methylene chloride (100 ml.) and triethylamine (1 ml.) were then added. The compound (1-trifluoromethyl)-2,2,2-trifluoroethyl chloroformate (8.3 g.) was added dropwise to the vigorously stirred reaction mixture over a 20-minute period while maintaining the temperature in the range of 25°–27° C. The reaction mixture was stirred for an additional 15 minutes. The two layers were separated and the aqueous layer was washed with methylene chloride (100 ml.). The resulting layers were separated and the organic layer was combined with the organic layer from the first separation. The combined organic layers were washed with two portions (100 ml. each) of 10% aqueous sodium hydroxide, one portion (199 ml.) of 10% hydrochloric acid, and dried over sodium sulfate. The solvent was removed on a rotary evaporator to give 12.4 g. of crude oil which crystallized. The product was recrystallized from diethyl ether—normal pentane to give 8.8 g. of crystals having a melting point of 62.5°–64.5° C. The infrared spectrum showed the carbonate ester absorption at 1795 cm$^{-1}$. The product was analyzed for carbon, hydrogen, and nitrogen. The results expressed in per cent by weight are shown in Table 7.

Table 7

| Analysis of 2',4'-dinitro-6'-sec-butylphenyl 1-(trifluoromethyl)-2,2,2-trifluoroethyl carbonate | | | |
|---|---|---|---|
| | C | H | N |
| Calculated for $C_{14}H_{12}F_6N_2O_7$ | 38.72 | 2.79 | 6.45 |
| First Analysis | 38.64 | 2.98 | 6.05 |
| Second Analysis | 38.83 | 2.96 | — |

The product may be depicted as having the structural formula:

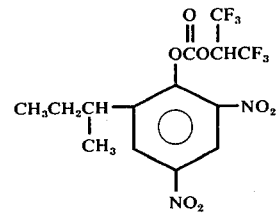

Example VIII

The sodium salt of 2,4-dinitro phenol was prepared by combining 2,4-dinitro phenol (7.3 g.), sodium hydroxide (2.4 g.), and water (150 ml.). Unstabilized methylene chloride (100 ml.) and triethylamine (1 ml.) were then added. The compound 2,2,3,3-tetrafluoropropyl chloroformate (8.5 g.) was added dropwise to the vigorously stirred reaction mixture over a 20-minute period while maintaining the temperature in the range of 24.5°–27.5° C. The reaction mixture was stirred for an additional 15 minutes. The two layers were separated and the aqueous layer was washed with methylene chloride (100 ml.). The resulting layer were separated and the organic layer was combined with the organic layer from the first separation. The combined organic layers were washed with two portions (100 ml. each) of 10% aqueous sodium hydroxide, one portion (100 ml.) of 10% hydrochloric acid and dried over sodium sulfate. The solvent was removed on a rotary evaporator to give 11.7 g. of oil which would not crystallize. The infrared spectrum showed the carbonate ester absorption at 1785 cm$^{-1}$. Purity was established to be about 92 percent by NMR spectroscopy.

The product may be depicted as having the structural formula:

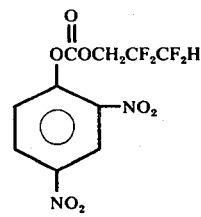

EXAMPLE IX

The sodium salt of 2,6-dinitro phenol was prepared by combining 2,6-dinitro phenol (7.6 g.) sodium hydroxide (2.4 g.), and water (157.6 ml.). Unstabilized methylene chloride (100 ml.) and triethylamine (1 ml.) were then added. The compound 2,2,3,3-tetrafluoropropyl chloroformate (8.5 g.) was added dropwise to the vigorously stirred reaction mixture over a 20-minute period while maintaining the temperature in the range of 25.5°–27.5° C. The reaction mixture was stirred for an additional 15 minutes. The two layers were separated and the aqueous layer was washed with methylene chloride (100 ml.). The resulting layers were separated and the organic layer was combined with the organic layer from the first separation. The combined organic layers were washed with two portions (100 ml. each) of 10% aqueous sodium hydroxide, one portion (100 ml.) of 10% hydrochloric acid, and dried over sodium sulfate. The solvent was removed on a rotary evaporator to give 11.1 g. of crude oil which crystallized. The product was recrystallized from diethyl ether—normal pentane to give 4.0 g. of crystals having a melting point of 68.5°–71.5° C. The infrared spectrum showed the carbonate ester absorption at 1790 cm$^{-1}$. The product was analyzed for carbon, hydrogen, and nitrogen. The results expressed in percent by weight are shown in Table 8.

Table 8

| Analysis of 2',6'-dinitrophenyl 2,2,3,3-tetrafluoropropyl carbonate | | | |
|---|---|---|---|
| | C | H | N |
| Calculated for $C_{10}H_6F_4N_2O_7$ | 35.10 | 1.77 | 8.19 |
| Found | 35.11 | 2.01 | 8.22 |

The product may be depicted as having the structural formula:

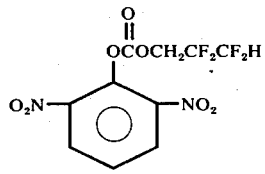

EXAMPLE X

Phosgen (296.7 g.) was condensed into anhydrous diethyl ether (200 ml.) contained in a one liter, four-necked, round-bottom flask equipped with a dropping funnel, a solid carbon dioxide condenser, a polytetrafluoroethylene blade paddle stirrer, a thermometer, and a phosgen inlet. The compound 2-fluoroethanol (96.1 g.) dissolved in an equal volume of diethyl ether was added in a stream to the mixture. Anhydrous pyridine (130.5 g.) dissolved in an equal volume of diethyl ether was added dropwise to the stirred reaction mixture while maintaining a temperature of 0° to 10° C. The dropwise addition of the pyridine was accomplished over a period of about one hour. The reaction mixture was stirred an additional hour at 0° to 10° C., then for two hours while gradually warming up to room temperature. The excess phosgene was removed from the reaction mixture. The precipitated pyridine hydrochloride was then removed by filtration and washed with diethyl ether. The diethyl ether wash was squeezed out of the paper into the filtrate. The filtrate was dried with sodium sulfate and diethyl ether solvent was removed by a one-plate distillation at atmospheric pressure. One-plate distillation at atmospheric pressure. One-plate distillation of the residue under reduced pressure gave product (93.7 g.) having an assay of 85.4 percent. The boiling point of the product, 2-fluoroethyl chloroformate, was 69° C. at 100 Torr.

The sodium salt of 2,4-dinitro-6-sec-butyl phenol was prepared by combining 2,4-dinitro-6-sec-butyl phenol (12.0 g.), sodium hydroxide (3.0 g.), and water (150 ml.). Unstabilized methylene chloride (100 ml.) and triethylamine (1 ml.) were then added. The compound 2-fluoroethyl chloroformate (6.9 g.) was added dropwise to the vigorously stirred reaction mixture over a 15-minute period while maintaining the temperature in the range of 27°–29° C. The reaction mixture was stirred for an additional 15 minutes. The two layers were separated and the aqueous layer was washed with methylene chloride (100 ml.). The resulting layers were separated and the organic layer was combined with the organic layer from the first separation. The combined organic layers were washed with two portions (100 ml. each) of 10% aqueous sodium hydroxide, one portion (100 ml.) of 10% hydrochloric acid and dried over sodium sulfate. The solvent was removed on a rotary evaporator to give 3.3 g. of crude oil which crystallized. The product was recrystallized from diethyl ether—normal pentane to give 1.9 g. of crystals having a melting point of 77.5°–80.5° C. The infrared spectrum showed the carbonate ester absorption at 1772 cm$^{-1}$. The product was analyzed for carbon, hydrogen and nitrogen. The results expressed in percent by weight are shown in Table 9.

Table 9

| Analysis of 2',4'-dinitro-6'-sec-butylphenyl 2-fluoroethyl carbonate | | | |
|---|---|---|---|
| | C | H | N |
| Calculated for $C_{13}H_{15}FN_2O_7$ | 47.28 | 4.58 | 8.48 |
| First Analysis | 47.84 | 4.91 | 8.63 |
| Second Analysis | 47.60 | 4.84 | — |

The product may be depicted as having the structural formula:

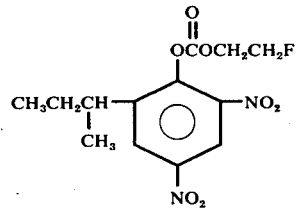

EXAMPLE XI

The sodium salt of 2,4-dinitro-6-tert-butyl phenol was prepared by combining 2,4-dinitro-6-tert-butyl phenol (7.2 g.), sodium hydroxide (1.8 g.), and water (150 ml.). Unstabilized methylene chloride (100 ml.) and triethylamine (1 ml.) were then added. The compound 2,2,3,3-tetrafluoropropyl chloroformate (6.4 g.) was added dropwise to the vigorously stirred reaction mixture over a 15-minute period while maintaining the temperature in the range of 23.5°–56.5° C. The reaction mixture was stirred for an additional 15 minutes. The two layers were separated and the aqueous layer was washed with methylene chloride (100 ml.). The resulting layers were separated and the organic layer was combined with the organic layer from the first separation. The combined organic layers were washed with two portions (100 ml. each) of 10% aqueous sodium hydroxide, one portion (100 ml.) of 10% hydrochloric acid, and dried over sodium sulfate. The solvent was removed on a rotary evaporator to give 8.7 g. of crude oil which crystallized. The product was recrystallized from diethyl ether—normal pentane to give 3.5 g.

of crystals having a melting point of 88.5°–91.5° C. The infrared spectrum showed the carbonate ester absorption at 1778 cm$^{-1}$. The product was analyzed for carbon, hydrogen and nitrogen. The results expressed in percent by weight are shown in Table 10.

Table 10

| Analysis of 2',4'-dinitro-6'-tert-butylphenyl 2,2,3,3-tetrafluoropropyl carbonate | | | |
|---|---|---|---|
| | C | H | N |
| Calculated for $C_{14}H_{14}F_4N_2O_7$ | 42.22 | 3.54 | 7.03 |
| First Analysis | 42.75 | 3.66 | 6.96 |
| Second Analysis | 42.38 | 3.66 | — |

The product may be depicted as having the structural formula:

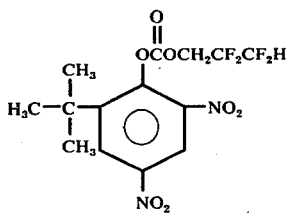

EXAMPLE XII

The sodium salt of 2,4-dinitro-6-cyclohexyl phenol was prepared by combining 2,4-dinitro-6-cyclohexyl phenol (12.0 g.), sodium hydroxide (2.7 g.), and water (150 ml.). Unstabilized methylene chloride (100 ml.) and triethylamine (1 ml.) were then added. The compound 2-fluoroethyl chloroformate (6.2 g.) was added dropwise to the vigorously stirred reaction mixture over a 25-minute period while maintaining the temperature in the range of 25°–27° C. The reaction mixture was stirred for an additional 15 minutes. The two layers were separated and the aqueous layer was washed with methylene chloride (100 ml.). The resulting layers were separated and the organic layer was combined with the organic layer from the first separation. The combined organic layers were washed with two portions (100 ml. each) of 10% aqueous sodium hydroxide, one portion (100 ml.) of 10% hydrochloric acid, and dried over sodium sulfate. The solvent was removed on a rotary evaporator to give 8.8 g. of crude oil which crystallized. The product was recrystallized from diethyl ether—normal pentane to yield 4.0 g. of crystals having a melting point range of 110.5° to 115.5° C. The infrared spectrum showed the carbonate ester absorption at 1772 cm$^{-1}$. The product was analyzed for carbon, hydrogen and nitrogen. The results expressed in percent by weight are shown in Table 11.

Table 11

| Analysis of 2',4'-dinitro-6'-cyclohexylphenyl 2-fluoroethyl carbonate | | | |
|---|---|---|---|
| | C | H | N |
| Calculated for $C_{15}H_{17}FN_2O_7$ | 50.56 | 4.81 | 7.86 |
| Found | 49.8 | 4.50 | 7.77 |

The product may be depicted as having the structural formula:

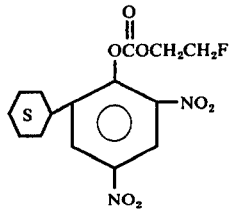

EXAMPLE XIII

The sodium salt of 2,4-dinitro-6-cyclohexyl phenol was prepared by combining 2,4-dinitro-6-cyclohexyl phenol (9.3 g.), sodium hydroxide (2.1 g.), and water (150 ml.). Unstabilized methylene chloride (100 ml.) and triethylamine (1 ml.) were then added. The compound 1-(trifluoromethyl)-2,2,2-trifluoroethyl chloroformate (8.8 g.) was added dropwise to the vigorously stirred reaction mixture over a 28-minute period while maintaining the temperature in the range of 25.5°–28° C. The reaction mixture was stirred for an additional 15 minutes. The two layers were separated and the aqueous layer was washed with methylene chloride (100 ml.). The resulting layers were separated and the organic layer was combined with the organic layer from the first separation. The combined organic layers were washed with two portions (100 ml. each) of 10% aqueous sodium hydroxide, one portion (100 ml.) of 10% hydrochloric acid, and dried over sodium sulfate. The solvent was removed on a rotary evaporator to give 8.3 g. of crude oil which crystallized. The product was recrystallized from diethyl ether—normal pentane to yield 5.9 g. of crystals having a melting point range of 131.5° to 135° C. The infrared spectrum showed the carbonate ester absorption at 1790 cm$^{-1}$. The product was analyzed for carbon, hydrogen and nitrogen. The results expressed in percent by weight are shown in Table 12.

Table 12

| Analysis of 2',4'-dinitro-6'-cyclohexylphenyl 1-(trifluoromethyl)-2,2,2-trifluoroethyl carbonate | | | |
|---|---|---|---|
| | C | H | N |
| Calculated for $C_{16}H_{14}F_6N_2O_7$ | 41.75 | 3.07 | 6.09 |
| Found | 41.5 | 2.86 | 6.13 |

The product may be depicted as having the structural formula:

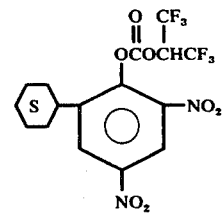

EXAMPLE XIV

The sodium salt of 2,4-dinitro-6-cyclohexyl phenol was prepared by combining 2,4-dinitro-6-cyclohexyl phenol (7.0 g.), sodium hydroxide (1.6 g.), and water (150 ml.). Unstabilized methylene chloride (100 ml.) and triethylamine (1 ml.) were then added. The compound 1H,1H,7H-dodecafluoroheptyl chloroformate (11.0 g.) was added dropwise to the vigorously stirred reaction mixture over a 30-minute period while maintaining the temperature in the range of 24.5°–26.5° C. The reaction mixture was stirred for an additional 15 minutes. The two layers were separated and the aqueous layer was washed with methylene chloride (100 ml.). The resulting layers were separated and the organic layer was combined with the organic layer from the first separation. The combined organic layers were washed with two portions (100 ml. each) of 10% aqueous sodium hydroxide, one portion (100 ml.) of 10% hydrochloric acid and dried over sodium sulfate. The solvent was removed on a rotary evaporator to give 14.4 g. of crude oil which crystallized. The product was recrystallized from diethyl ether—normal pentane to yield 6.5 g. of crystals having a melting point range of 68.5° to 72° C. The infrared spectrum showed the carbonate ester absorption at 1780 cm$^{-1}$. The product was analyzed for carbon, hydrogen and nitrogen. The results expressed in percent by weight are shown in Table 13.

Table 13

| Analysis of 2',4'-dinitro-6'-cyclohexylphenyl 1H,1H,7H-dodecafluoroheptyl carbonate | | | |
|---|---|---|---|
| | C | H | N |
| Calculated for C$_{20}$H$_{16}$F$_{12}$N$_2$O$_7$ | 38.47 | 2.58 | 4.49 |
| Found | 38.2 | 2.33 | 4.53 |

The product may be depicted as having the structural formula:

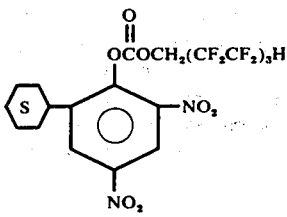

EXAMPLE XV

The sodium salt of 2,4-dinitro-6-cyclohexyl phenol was prepared by combining 2,4-dinitro-6-cyclohexyl phenol (5.3 g.), sodium hydroxide (1.2 g.) and water (150 ml.). Unstabilized methylene chloride (100 ml.) and triethylamine (1 ml.) were then added. The compound 1H,1H,11H-eicosafluoroundecyl chloroformate (13.0 g.) was added dropwise to the vigorously stirred reaction mixture over a 25 minute period while maintaining the temperature in the range of 24°–25° C. The reaction mixture was stirred for an additional 15 minutes. The two layers were separated and the aqueous layer was washed with methylene chloride (100 ml.). The resulting layers were separated and the organic layer was combined with the organic layer from the first separation. The combined organic layers were washed with two portions (100 ml. each) of 10% aqueous sodium hydroxide, one portion (100 ml.) of 10% hydrochloric acid and dried over sodium sulfate. The solvent was removed on a rotary evaporator to give 9.6 g. of crude oil which crystallized. The product was recrystallized from diethyl ether—normal pentane to yield 5.8 g. of crystals having a melting point range of 119° to 123° C. The infrared spectrum showed the carbonate ester absorption at 1780 cm$^{-1}$. The product was analyzed for carbon, hydrogen and nitrogen. The results expressed in percent by weight are shown in Table 14.

Table 14

| Analysis of 2',4'-dinitro-6'-cyclohexylphenyl 1H,1H,11H-eicosafluoroundecyl carbonate | | | |
|---|---|---|---|
| | C | H | N |
| Calculated for C$_{24}$H$_{16}$F$_{20}$N$_2$O$_7$ | 34.96 | 1.96 | 3.40 |
| Found | 33.7 | 1.74 | 3.25 |

The product may be depicted as having the structural formula:

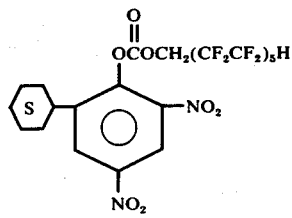

Many of the fluorinated alcohols used to prepare the precursor chloroformates and many of the substituted phenols are known to the art. In those instances where the compounds having the desired substituents are not available, they may be prepared by any of the methods well known in chemistry. In the case of compounds falling within the scope of formula (III) a particularly advantageous method is available for preparing the precursor alcohol which consists in reacting methanol with one or more equivalents of tetrafluoroethylene in the presence of a free radical initiator. The over-all equation for the reaction is:

$$HOCH_3 + nCF_2=CF_2 \rightarrow HOCH_2(CF_2CF_2)_nH$$

More specific details of this reaction may be found in U.S. Pat. Nos. 2,959,611 and 2,559,628. The 1,1-dihydroperfluoroalkyl alcohols and their preparation are described in U.S. Pat. No. 2,666,797. The reaction between fluoro alcohols and phosgene to form chloroformates is described in U.S. Pat. No. 2,959,611. The preparation of perfluoroalkyl chloroformates from perfluoroalkyl hypochlorites is described by Young et al., "Perfluoroalkyl Chloroformates and Chlorosulfates," Tetrahedron Letters, No. 9 (1969) Pergamon Press, pp. 723–726. The fluorinated alkenyl chloroformates and fluorinated alkynyl chloroformates may be prepared by methods analogous to those for preparing the fluorinated alkyl chloroformates.

In general, the carbonates of this invention may be used to kill or retard development of mites.

In one embodiment the carbonate is applied directly to the mites. In another embodiment the carbonate is applied to regions where mites are likely to be found in order to kill the mites present or to preclude mite populations from becoming established.

Usually formulations containing from about 5 to about 2,000 parts per million by weight (ppm) of the carbonate compound are applied. Typical formulations contain from about 10 to about 1,000 ppm. Often formulations containing from about 10 to about 100 ppm are used.

The type of formulation used may vary. Solutions and suspensions of the carbonate are effective. The usual method of applying solutions or suspensions is to drench the area of application. Sprays, showers, mists, and dips may be used for this purpose. When some of the more active carbonates are used, particularly at higher concentrations, a complete drenching is not necessary. Mists are often used where a drench is not desired.

The carbonate formulations of the invention may also be applied in the form of a powder or dust. These powders or dusts may contain diluents such as, for example, aluminum silicate, bentonite, calcium carbonate, calcium silicate, diatomaceous silica, hydrated lime, pulverized limestone, montmorillonite, pulverized phosphate rock, silica, talc, or vermiculite.

The concentration of the carbonate compound in the formulation and the total amount applied will vary depending upon the particular carbonate being employed and the particular mite being confronted. Other factors such as season of the year, environmental conditions, and stage of mite development all have their effect.

The following specific embodiments illustrate, by way of example, the basic principles of the present invention:

EXAMPLE XVI

Potted horticultural bean plants (*Phaseolus vulgaris*, L.) at growth stage when primarily leaves are approximately 1 inch long are infested with two-spotted spider mites (*Tetranychus urticae*) 24 hours prior to treatment, insuring establishment of adults and deposition of eggs at the time of treatment.

When possible, the test compounds are formulated as follows: A stock acetone emulsion is prepared having the following composition by weight: 99.75 percent acetone, 0.20 percent sorbitan trioleate (Span 85), and 0.05 percent sorbitan monooleate polyoxyalkylene derivative (Tween 80). Test compound is dissolved in a portion of the stock acetone emulsion. Deionized water is added to yield a concentrated test solution containing about 10 percent acetone, 0.020 percent Span 85 and 0.0050 percent Tween 80. The amount of test compound dissolved in the stock acetone emulsion is such that when diluted with deionized water the concentrated test solution has the highest concentration (usually 1,000 ppm) of test compound used in the tests. Other solutions are prepared by diluting the concentrated test solution with a mixture of deionized water and stock acetone emulsion, which mixture contains about 10 percent acetone, 0.020 percent Span 85, and 0.0050 percent Tween 80. Thus, all test solutions always contain about 10 percent acetone, 0.020 percent Span 85, and 0.0050 percent Tween 80, irrespective of the concentration of test compound. Compounds giving an unsatisfactory formulation as an acetone emulsion are formulated as wet-table powders and diluted with water and wetting agent before application.

Infested host plants are dipped into agitated solutions of the test compound, allowed to air dry, provided with a subterranean water source, and held for observation. Three test plants are used for each unit of treatment.

Initial mortality is determined 48 to 72 hours after treatment by removing and observing one leaf from each plant. Final observations of mortality, ovicidal action, and residual toxicity to emerging nymphs are made 7 days after treatment by removal and observation of the second primary leaf. The observed results are reported in terms of Percent Mortality. Table 15 reports observed results where the test compound is 2',4'-dinitro-6'-secbutylphenyl 2,2,2-trifluoroethyl carbonate.

Table 15

Miticidal Effectiveness of 2',4'-Dinitro-6'-sec-butylphenyl 2,2,2-Trifluoroethyl Carbonate Against Two-Spotted Spider Mite (*Tetranychus urticae*)

| Concentration ppm | Per Cent Mortality | | |
|---|---|---|---|
| | Initial | Ovicidal | Residual |
| 1,000 | 100 | 100 | No Young |
| 500 | 100 | 90 | 100 |
| 250 | 100 | 75 | 99 |
| 100 | 75 | 0, Trace, 83 | 94, Trace |
| 50 | — | 0, 48 | 0 |
| 25 | — | 0, 20 | 0 |

EXAMPLE XVII

The procedure of Example XVI is repeated except that the test compound is 2',4'-dinitro-6'-sec-butylphenyl 2,2,3,3-tetrafluoropropyl carbonate. Table 16 reports the observed results of this test.

Table 16

Miticidal Effectiveness of 2',4'-Dinitro-6'-butylphenyl 2,2,3,3-Tetrafluoropropyl Carbonate Against Two-Spotted Spider Mite (*Tetranychus urticae*)

| Concentration ppm | Per Cent Mortality | | |
|---|---|---|---|
| | Initial | Ovicidal | Residual |
| 1,000 | 100 | 100 | No Young |
| 500 | 100 | 100 | No Young |
| 250 | 100 | 100 | No Young |
| 100 | 100 | 10 | 0 |
| 50 | 100 | — | — |
| 25 | 100 | — | — |
| 10 | 41 | — | — |

EXAMPLE XVIII

The procedure of Example XVI is repeated except that the test compound is 2',4'-dinitro-6'-cyclohexylphenyl 2,2,3,3-tetrafluoropropyl carbonate. Table 17 reports the observed results of this test.

Table 17

Miticidal Effectiveness of 2',4'-Dinitro-6'-cyclohexylphenyl 2,2,3,3-Tetrafluoropropyl Carbonate Against Two-Spotted Spider Mite (*Tetranychus urticae*)

| Concentration ppm | Per Cent Mortality | | |
|---|---|---|---|
| | Initial | Ovicidal | Residual |
| 1,000 | 88 | Trace | 90 |
| 50 | 24 | 0 | 0 |
| 25 | 5 | 0 | 0 |
| 10 | 8 | 0 | 0 |

EXAMPLE XIX

The procedure of Example XVI is repeated except that the test compound is 2',4'-dinitro-6'-methylphenyl 2,2,3,3-tetrafluoropropyl carbonate. Table 18 reports the observed results of this test.

Table 18

Miticidal Effectiveness of 2',4'-Dinitro-6'-methylphenyl 2,2,3,3-Tetrafluoropropyl Carbonate Against Two-Spotted Spider Mite (*Tetranychus urticae*)

| Concentration ppm | Per Cent Mortality | | |
|---|---|---|---|
| | Initial | Ovicidal | Residual |
| 1,000 | 100 | 0 | 0 |
| 50 | 16 | 0 | 0 |
| 25 | 8 | 0 | 0 |
| 10 | 8 | 0 | 0 |

EXAMPLE XX

The procedure of Example XVI is repeated except that the test compound is 2',4'-dinitro-6'-sec-butylphenyl 1H,1H,11H-eicosafluoroundecyl carbonate. Table 19 reports the observed results of this test.

Table 19

Miticidal Effectiveness of 2',4'-Dinitro-6'-sec-butylphenyl 1H,1H,11H-Eicosafluoroundecyl Carbonate Against Two-Spotted Spider Mite (*Tetranychus urticae*)

| Concentration ppm | Per Cent Mortality | |
|---|---|---|
| | Initial | Ovicidal |
| 1,000 | 97 | 0 |
| 500 | 87 | 25 |
| 250 | 25 | Trace |
| 100 | 19 | 0 |

EXAMPLE XXI

The procedure of Example XVI is repeated except that the test compound is 2',4'-dinitro-6'-sec-butylphenyl 1-trifluoromethyl-2,2,2-trifluoromethyl carbonate. Table 20 reports the observed results of this test.

Table 20

Miticidal Effectiveness of 2',4'-Dinitro-6'-sec-butylphenyl 1-(Trifluoromethyl)-2,2,2-trifluoroethyl Carbonate Against Two-Spotted Spider Mite (*Tetranychus urticae*)

| Concentration ppm | Per Cent Mortality | |
|---|---|---|
| | Initial | Ovicidal |
| 1,000 | 100 | 100 |
| 500 | 100 | 100 |
| 250 | 100 | 90 |
| 100 | 100 | 60 |
| 50 | 100 | 55 |
| 25 | 100 | Trace |
| 10 | 50 | 0 |
| 5 | 10 | 0 |

EXAMPLE XXII

The procedure of Example XVI is repeated except that the test compound is 2',4'-dinitrophenyl 2,2,3,3-tetrafluoropropyl carbonate. Table 21 reports the observed results of this test.

Table 21

Miticidal Effectiveness of 2',4'-Dinitrophenyl 2,2,3,3-Tetrafluoropropyl Carbonate Against Two-Spotted Spider Mite (*Tetranychus urticae*)

| Concentration ppm | Per Cent Mortality | |
|---|---|---|
| | Initial | Ovicidal |
| 1,000 | 100 | 80 |
| 500 | 63 | Trace |
| 250 | 14 | 0 |
| 100 | 4 | 0 |

EXAMPLE XXIII

The procedure of Example XVI is repeated except that the test compound is 2',6'-dinitrophenyl 2,2,3,3-tetrafluoropropyl carbonate. Table 22 reports the observed results of this test.

Table 22

Miticidal Effectiveness of 2',6'-Dinitrophenyl 2,2,3,3-Tetrafluoropropyl Carbonate Against Two-Spotted Spider Mite (*Tetranychus urticae*)

| Concentration ppm | Per Cent Mortality | |
|---|---|---|
| | Initial | Ovicidal |
| 1,000 | 26 | 0 |

EXAMPLE XXIV

The procedure of Example XVI is repeated except that the test compound is 2',4'-dinitro-6'-sec-butylphenyl 2-fluoroethyl carbonate. Table 23 reports the observed results of this test.

Table 23

Miticidal Effectiveness of 2',4'-Dinitro-6'-sec-butylphenyl 2-Fluoroethyl Carbonate Against Two-Spotted Spider Mite (*Tetranychus urticae*)

| Concentration ppm | Per Cent Mortality | |
|---|---|---|
| | Initial | Ovicidal |
| 1,000 | 100 | 100 |
| 500 | 100 | 100 |
| 250 | 100 | 100 |
| 100 | 100 | 99 |
| 50 | 85 | 100 |
| 25 | 30 | 20 |
| 10 | 8 | Trace |
| 5 | 6 | 0 |

EXAMPLE XXV

The procedure of Example XVI is repeated except that the test compound is 2',4'-dinitro-6'-tert-butylphenyl 2,2,3,3-tetrafluoropropyl carbonate. Table 24 reports the observed results of this test.

Table 24

Miticidal Effectiveness of 2',4'-Dinitro-6'-tert-butylphenyl 2,2,3,3-Tetrafluoropropyl Carbonate Against Two-Spotted Spider Mite (*Tetranychus urticae*)

| Concentration ppm | Per Cent Mortality | |
|---|---|---|
| | Initial | Ovicidal |
| 1,000 | 100 | 100 |
| 500 | 100 | 80 |
| 250 | 95 | Trace |
| 100 | 66 | 0 |

EXAMPLE XXVI

The procedure of Example XVI is repeated except that the test compound is 2',4'-dinitro-6'-sec-butylphenyl 1H,1H,7H-dodecafluoroheptyl carbonate. Table 25 reports the observed results of this test.

Table 25

Miticidal Effectiveness of 2',4'-Dinitro-6'-sec-butylphenyl 1H,1H,7H-Dodecafluoroheptyl Carbonate Against Two-Spotted Spider Mite (*Tetranychus urticae*)

| Concentration ppm | Per Cent Mortality | |
|---|---|---|
| | Initial | Ovicidal |
| 1,000 | 100 | 45 |
| 500 | 100 | 70 |
| 250 | 100 | 30 |
| 100 | 53 | Trace |

Many of the carbonates of the present invention possess properties which make them useful as phytocides, as for example, herbicides. Weeds may be killed by applying to the soil in the vicinity of the weeds a phytocidal amount of the carbonate. Weeds may also be killed by bringing a phytocidal amount of the carbonate and the weeds into mutual contact, as for example, by applying the carbamate directly to the weeds. In another embodiment the carbonate is applied to the soil where weeds are likely to be found in order to preclude weeds from becoming established.

The formulations used as phytocides are similar in all material respects to those described above for miticidal purposes. The concentration of the carbonate compound in the formulation and the total amount applied will vary depending upon the particular carbonate being employed and the particular weed being confronted. Other factors such as season of the year, environmental conditions and stage of weed development all have their effect. Exemplary application rates are from about 0.1 to about 100 pounds per acre. Usually the rate will range from about 0.1 to about 20 pounds per acre. Rates of from about 0.5 to about 10 pounds per acre are most often used.

In Examples XXVII through LI the following procedure was used: For pre-emergence testing, appropriate weed species are seeded in individual disposable three-inch square containers containing about 2 inches of soil. After spraying directly on the seeded soil surface, a small amount of sand, usually about 1/8 to 1/4 inch in depth, is applied to cover the seeds.

For post-emergence testing, appropriate weed species are seeded by growth-time requirement schedules in individual disposable 3 inch square containers containing about 2 inches of soil, watered as required, and maintained under greenhouse conditions. When all weeds have reached suitable growth development, generally first true leaf stage, plants appropriate to pertaining test requirements are selected for uniformity of growth and development. One container of each weed, averaging up to 50 plants per individual container, is then placed on a carrying tray for treatment.

When possible, the test compounds are formulated in a solvent mixture of 90% acetone, 8% methanol, and 2% dimethylformamide by volume. Insoluble compounds are formulated as wettable powders and diluted with water and wetting agent before application.

Each carrying tray of pre-emergence and/or post emergence containers, placed on a conveyor belt having a linear speed of 1.5 miles per hour, trips a microswitch which, in turn, activates a solenoid valve and releases the compound under test. The compound under test is discharged as sprays at a rate of 50 gallons per acre. Containers for both pre-emergence and post-emergence testing are then removed to the greenhouse and held for observation.

Pre-emergence and post-emergence treatments are observed daily for interim response, final observations usually being made 14 days after treatment. Any treatments inducing significant response are held beyond the 14-day observation period until such responses can be confirmed. Each result is reported as an Injury Rating which is represented as follows: 0 — no visible effect; 1, 2, 3 — slight injury, plant usually recovered with little or no reduction in top growth; 4, 5, or 6 — moderate injury, plants usually recovered but with reduced top growth; 7, 8, or 9 — severe injury, plants usually did not recover; 10 — all plants killed. Deviations from the above procedure, if any, are reported with the data.

EXAMPLE XXVII

Test Compound: 2',4'-Dinitro-6'-sec-butylphenyl 2,2,2-trifluoroethyl carbonate

Pre-Emergence Observations made 21 days after application
Post-Emergence Observations made 9 days after application

| Test Plant | Pre-Emergence 10 lb./A | Post-Emergence 10 lb./A |
|---|---|---|
| Yellow Nutsedge (*Cyperus esculentus* L.) | 0 | 0 |

EXAMPLE XXVII-continued

Test Compound: 2',4'-Dinitro-6'-sec-butylphenyl 2,2,2-trifluoroethyl carbonate

Pre-Emergence Observations made 21 days after application
Post-Emergence Observations made 9 days after application

| Test Plant | Pre-Emergence 10 lb./A | Post-Emergence 10 lb./A |
|---|---|---|
| Wild Oats (*Avena fatua* L.) | 8 | 10 |
| Jumsonweed (*Datura stramonium* L.) | 10 | 10 |
| Velvetleaf (*Abutilon theophrasti* Medic.) | 8 | 10 |
| Johnsongrass (*Sorghum halepense* Pers.) | 1 | 3 |
| Lamsquarter (*Chenopodium album* L.) | 10 | — |
| Mustard (*Brassica kaber* L. C. Wheeler Var. *pinnatifida* L. C. Wheeler | 10 | 10 |
| Yellow Foxtail (*Setaria glauca* Beauv.) | 0 | 0 |
| Barnyardgrass (*Echinochloa crusgalli* Beauv.) | 1 | 2 |
| Crabgrass (*Digitaria sanguinalis* Scop.) | 2 | 3 |
| Buckwheat (*Polygonum convolvulus* L.) | 9 | 10 |
| Morning Glory (mixture of *Ipomoea purpurea* Roth and *Ipomoea hederacea* Jacq.) | 8 | 10 |
| Red Kidney Bean (*Phaseolus vulgaris* L.) | — | 3 |
| Untreated Controls | Normal | Normal |

EXAMPLE XXVIII

Test Compound: 2',4'-Dinitro-6'-sec-butylphenyl 2,2,2-trifluoroethyl carbonate

Observations made 16 days after application

| Test Plant | Pre-Emergence 5 lb/A | 2.5 lb/A | 1.25 lb/A |
|---|---|---|---|
| Yellow Nutsedge (*Cyperus esculentus* L.) | 0 | 0 | 0 |
| Wild Oats (*Avena fatua* L.) | 1 | 0 | 0 |
| Jimsonweed (*Datura stramonium* L.) | 9 | 8 | 8 |
| Velvetleaf (*Abutilon theophrasti* Medic.) | 9 | 8 | 0 |
| Johnsongrass (*Sorghum halepense* Pers.) | 0 | 0 | 0 |
| Lambsquarter (*Chenopodium album* L.) | 10 | 10 | 10 |
| Mustard (*Brassica kaber* L. C. Wheeler Var. *pinnatifida* L. C. Wheeler) | 10 | 10 | 9 |
| Yellow Foxtail (*Setaria glauca* Beauv.) | 2 | 0 | 0 |
| Barnyardgrass (*Echinochloa crusgalli* Beauv.) | 3 | 0 | 0 |
| Crabgrass (*Digitaria sanguinalis* Scop.) | 2 | 0 | 0 |
| Buckwheat (*Polygonum convolvulus* L.) | 9 | 9 | 9 |
| Morning Glory (mixture of *Ipomoea purpurea* Roth and *Ipomoea hederacea* Jacq.) | 2 | 4 | 1 |
| Untreated Controls | Normal | Normal | Normal |

EXAMPLE XXIX

Test Compound: 2',4'-Dinitro-6'-sec-butylphenyl 2,2,2-trifluoroethyl carbonate

Observations made 21 days after application

| Test Plant | Pre-Emergence 5 lb/A | 2.5 lb/A | 1.25 lb/A |
|---|---|---|---|
| Yellow Nutsedge (*Cyperus esculentus* L.) | 0 | 0 | 0 |
| Wild Oats (*Avena fatua* L.) | 0 | 0 | 0 |
| Jimsonweed (*Datura stramonium* L.) | 10 | 10 | 10 |
| Velvetleaf (*Abutilon theophrasti* Medic.) | 10 | 10 | 0 |
| Johnsongrass (*Sorghum halepense* Pers.) | 0 | 0 | 0 |
| Lambsquarter (*Chenopodium album* L.) | 10 | 10 | 5 |
| Mustard (*Brassica kaber* L. C. Wheeler Var. *pinnatifida* L. C. Wheeler) | 10 | 10 | 10 |
| Yellow Foxtail (*Setaria glauca* Beauv.) | 2 | 0 | 0 |
| Barnyardgrass (*Echinochloa crusgalli* Beauv.) | 3 | 0 | 0 |
| Crabgrass (*Digitaria sanguinalis* Scop.) | 2 | 0 | 0 |
| Buckwheat (*Polygonum convolvulus* L.) | 10 | 10 | 9 |
| Morning Glory (mixture of *Ipomoea purpurea* Roth and *Ipomoea hederacea* Jacq.) | 2 | 4 | 2 |

EXAMPLE XXIX-continued

Test Compound: 2',4'-Dinitro-6'-sec-butylphenyl 2,2,2-trifluoroethyl carbonate

Observations made 21 days after application

| Test Plant | Pre-Emergence 5 lb/A | 2.5 lb/A | 1.25 lb/A |
|---|---|---|---|
| Untreated Controls | Normal | Normal | Normal |

EXAMPLE XXX

Test Compound: 2',4'-Dinitro-6'-sec-butylphenyl 2,2,2-trifluoroethyl carbonate

Observations made 13 days after application

| Test Plant | Post-Emergence 5 lb/A | 2.5 lb/A | 1.25 lb/A |
|---|---|---|---|
| Yellow Nutsedge (Cyperus esculentus L.) | 2 | 0 | 0 |
| Wild Oats (Avena fatua L.) | 3 | 2 | 1 |
| Jimsonweed (Datura stramonium L.) | 10 | 10 | 10 |
| Velvetleaf (Abutilon theophrasti Medic.) | 10 | 10 | 10 |
| Johnsongrass (Sorghum halepense Pers.) | 0 | 0 | 0 |
| Mustard (Brassica kaber L. C. Wheeler Var. pinnatifida L. C. Wheeler) | 10 | 10 | 10 |
| Yellow Foxtail (Setaria glauca Beauv.) | 0 | 0 | 0 |
| Barnyardgrass (Echinochloa crusgalli Beauv.) | 0 | 0 | 0 |
| Crabgrass (Digitaria sanguinalis Scop.) | 0 | 0 | 0 |
| Buckwheat (Polygonum convolvulus L.) | 10 | 10 | 10 |
| Morning Glory (mixture of Ipomoea purpurea Roth and Ipomoea hederacea Jacq.) | 10 | 10 | 7 |
| Red Kidney Bean (Phaseolus vulgaris L.) | | | |
| Primary Leaf Stage | 0 | 0 | 0 |
| Trifoliate Leaf Stage | 1 | 1 | 1 |
| Untreated Controls | Normal | Normal | Normal |

EXAMPLE XXXI

Test Compound: 2',4'-Dinitro-6'-sec-butylphenyl 2,2,3,3-tetrafluoropropyl carbonate Pre-Emergence Observations made 21 days after application.
Post-Emergence Observations made 9 days after application.

| Test Plant | Pre-Emergence 10 lb./A | Post-Emergence 10 lb./A |
|---|---|---|
| Yellow Nutsedge (Cyperus esculentus L.) | 0 | 1 |
| Wild Oats (Avena fatua L.) | 6 | 10 |
| Jimsonweed (Datura stramonium L.) | 10 | 10 |
| Velvetleaf (Abutilon theophrasti Medic.) | 10 | 10 |
| Johnsongrass (Sorghum halepense Pers.) | 0 | 2 |
| Lambsquarter (Chenopodium album L.) | 10 | — |
| Mustard (Brassica kaber L. C. Wheeler Var. pinnatifida L. C. Wheeler) | 10 | 10 |
| Yellow Foxtail (Setaria glauca Beauv.) | 0 | 2 |
| Barnyardgrass (Echinochloa crusgalli Beauv.) | 1 | 3 |
| Crabgrass (Digitaria sanguinalis Scop.) | 7 | 2 |
| Buckwheat (Polygonum convolvulus L.) | 8 | 10 |
| Morning Glory (mixture of Ipomoea purpurea Roth and Ipomoea hederacea Jacq.) | 8 | 10 |
| Red Kidney Bean (Phaseolus vulgaris L.) | — | 0 |
| Untreated Controls | Normal | Normal |

EXAMPLE XXXII

Test Compound: 2',4'-Dinitro-6'-sec-butylphenyl 2,2,3,3-tetrafluoropropyl carbonate Observations made 16 days after application

| Test Plant | Pre-Emergence 5 lb/A | 2.5 lb/A | 1.25 lb/A |
|---|---|---|---|
| Yellow Nutsedge (Cyperus esculentus L.) | 0 | 0 | 0 |
| Wild Oats (Avena fatua L.) | 0 | 0 | 0 |
| Jimsonweed (Datura stramonium L.) | 9 | 9 | 8 |

EXAMPLE XXXII-continued

Test Compound: 2',4'-Dinitro-6'-sec-butylphenyl 2,2,3,3-tetrafluoropropyl carbonate Observations made 16 days after application

| Test Plant | Pre-Emergence 5 lb/A | 2.5 lb/A | 1.25 lb/A |
|---|---|---|---|
| Velvetleaf (Abutilon theophrasti Medic.) | 9 | 9 | 9 |
| Johnsongrass (Sorghum halepense Pers.) | 0 | 0 | 0 |
| Lambsquarter (Chenopodium album L.) | 10 | 10 | 10 |
| Mustard (Brassica kaber L. C. Wheeler Var. pinnatifida L. C. Wheeler) | 10 | 10 | 10 |
| Yellow Foxtail (Setaria glauca Beauv.) | 2 | 0 | 0 |
| Barnyardgrass (Echinochloa crusgalli Beauv.) | 2 | 0 | 0 |
| Crabgrass (Digitaria sanguinalis Scop.) | 3 | 0 | 0 |
| Buckwheat (Polygonum convolvulus L.) | 8 | 8 | 8 |
| Morning Glory (mixture of Ipomoea purpurea Roth and Ipomoea hederacea Jacq.) | 5 | 1 | 1 |
| Untreated Controls | Normal | Normal | Normal |

EXAMPLE XXXIII

Test Compound: 2',4'-Dinitro-6'-sec-butylphenyl 2,2,3,3-tetrafluoropropyl carbonate Observations made 21 days after application

| Test Plant | Pre-Emergence 5 lb/A | 2.5 lb/A | 1.25 lb/A |
|---|---|---|---|
| Yellow Nutsedge (Cyperus esculentus L.) | 0 | 0 | 0 |
| Wild Oats (Avena fatua L.) | 0 | 0 | 0 |
| Jimsonweed (Datura stramonium L.) | 10 | 9 | 9 |
| Velvetleaf (Abutilon theophrasti Medic.) | 9 | 8 | 8 |
| Johnsongrass (Sorghum halepense Pers.) | 0 | 0 | 0 |
| Lambsquarter (Chenopodium album L.) | 10 | 10 | 5 |
| Mustard (Brassica kaber L. C. Wheeler Var. pinnatifida L. C. Wheeler) | 10 | 10 | 10 |
| Yellow Foxtail (Setaria glauca Beauv.) | 0 | 0 | 0 |
| Barnyardgrass (Echinochloa crusgalli Beauv.) | 2 | 0 | 0 |
| Crabgrass (Digitaria sanguinalis Scop.) | 2 | 0 | 0 |
| Buckwheat (Polygonum convolvulus L.) | 10 | 8 | 8 |
| Morning Glory (mixture of Ipomoea purpurea Roth and Ipomoea hederacea Jacq.) | 4 | 2 | 0 |
| Untreated Controls | Normal | Normal | Normal |

EXAMPLE XXXIV

Test Compound: 2',4'-Dinitro-6'-sec-butylphenyl 2,2,3,3-tetrafluoropropyl carbonate Observations made 13 days after application

| Test Plant | Post-Emergence 5 lb/A | 2.5 lb/A | 1.25 lb/A |
|---|---|---|---|
| Yellow Nutsedge (Cyperus esculentus L.) | 2 | 0 | 0 |
| Wild Oats (Avena fatua L.) | 8 | 6 | 4 |
| Jimsonweed (Datura stramonium L.) | 10 | 10 | 10 |
| Velvetleaf (Abutilon theophrasti Medic.) | 10 | 10 | 10 |
| Johnsongrass (Sorghum halepense Pers.) | 3 | 1 | 0 |
| Mustard (Brassica kaber L. C. Wheeler Var. pinnatifida L. C. Wheeler) | 10 | 10 | 10 |
| Yellow Foxtail (Setaria glauca Beauv.) | 1 | 0 | 0 |
| Barnyardgrass (Echinochloa crusgalli Beauv.) | 8 | 4 | 2 |
| Crabgrass (Digitaria sanguinalis Scop.) | 1 | 0 | 0 |
| Buckwheat (Polygonum convolvulus L.) | 10 | 10 | 10 |
| Morning Glory (mixture of Ipomoea purpurea Roth and Ipomoea hederacea Jacq.) | 10 | 10 | 9 |
| Red Kidney Bean (Phaseolus vulgaris L.) | | | |

EXAMPLE XXXIV-continued

Test Compound: 2',4'-Dinitro-6'-sec-butylphenyl 2,2,3,3-tetrafluoropropyl carbonate Observations made 13 days after application

| Test Plant | Post-Emergence | | |
|---|---|---|---|
| | 5 lb/A | 2.5 lb/A | 1.25 lb/A |
| Primary Leaf Stage | 1 | 0 | 0 |
| Trifoliate Leaf Stage | 0 | 0 | 0 |
| Untreated Controls | Normal | Normal | Normal |

EXAMPLE XXXV

Test Compound: 2',4'-Dinitro-6'-cyclohexylphenyl 2,2,3,3-tetrachloropropyl carbonate Pre-Emergence Observations made 13 days after application
Post-Emergence Observations made 14 days after application

| Test Plant | Pre-Emergence 10 lb./A | Post-Emergence 10 lb./A |
|---|---|---|
| Yellow Nutsedge (Cyperus esculentus L.) | 0 | 0 |
| Wild Oats (Avena fatua L.) | 0 | 2 |
| Jimsonweed (Datura stramonium L.) | 0 | 10 |
| Velvetleaf (Abutilon theophrasti Medic.) | 0 | 0 |
| Johnsongrass (Sorghum halepense Pers.) | 0 | 0 |
| Pigweed (Amaranthus retroflexus L.) | 9 | — |
| Mustard (Brassica kaber L. C. Wheeler Var. pinnatifida L. C. Wheeler) | 7 | 10 |
| Yellow Foxtail (Setaria glauca Beauv.) | 0 | 0 |
| Barnyardgrass (Echinochloa crusgalli Beauv.) | 0 | 1 |
| Crabgrass (Digitaria sanguinalis Scop.) | 0 | 0 |
| Buckwheat (Polygonum convolvulus L.) | 0 | 9 |
| Morning Glory (mixture of Ipomoea purpurea Roth and Ipomoea hederacea Jacq.) | 0 | 0 |
| Red Kidney Bean (Phaseolus vulgaris L.) | | |
| Primary Leaf Stage | — | 0 |
| Trifoliate Leaf Stage | — | 0 |
| Untreated Controls | Normal | Normal |

EXAMPLE XXXVI

Test Compound: 2',4'-Dinitro-6'-methylphenyl 2,2,3,3-tetrafluoropropyl carbonate Pre-Emergence Observations made 13 days after application
Post-Emergence Observations made 14 days after application

| Test Plant | Pre-Emergence 10 lb./A | Post-Emergence 10 lb./A |
|---|---|---|
| Yellow Nutsedge (Cyperus esculentus L.) | 0 | 0 |
| Wild Oats (Avena fatua L.) | 1 | 9 |
| Jimsonweed (Datura stramonium L.) | 0 | 10 |
| Velvetleaf (Abutilon theophrasti Medic.) | 0 | 10 |
| Johnsongrass (Sorghum halepense Pers.) | 2 | 0 |
| Pigweed (Amaranthus retroflexus L.) | 9 | — |
| Mustard (Brassica kaber L. C. Wheeler Var. pinnatifida L. C. Wheeler) | 8 | 10 |
| Yellow Foxtail (Setaria glauca Beauv.) | 2 | 0 |
| Barnyardgrass (Echinochloa crusgalli Beauv.) | 0 | 7 |
| Crabgrass (Digitaria sanguinalis Scop.) | 3 | 8 |
| Buckwheat (Polygonum convolvulus L.) | 4 | 10 |
| Morning Glory (mixture of Ipomoea purpurea Roth and Ipomoea hederacea Jacq.) | 6 | 8 |
| Red Kidney Bean (Phaseolus vulgaris L.) | | |
| Primary Leaf Stage | — | 1 |
| Trifoliate Leaf Stage | — | 0 |
| Untreated Controls | Normal | Normal |

EXAMPLE XXXVII

Test Compound: 2',4'-Dinitro-6'-methylphenyl 2,2,3,3-tetrafluoropropyl carbonate Observations made 21 days after application

| Test Plant | Pre-Emergence 10 lb./A |
|---|---|
| Yellow Nutsedge (Cyperus esculentus L.) | 0 |
| Wild Oats (Avena fatua L.) | 1 |
| Jimsonweed (Datura stramonium L.) | 0 |
| Velvetleaf (Abutilon theophrasti Medic.) | 0 |
| Johnsongrass (Sorghum halepense Pers.) | 0 |
| Pigweed (Amaranthus retroflexus L.) | 9 |
| Mustard (Brassica kaber L. C. Wheeler Var. pinnatifida L. C. Wheeler) | 9 |
| Yellow Foxtail (Setaria glauca Beauv.) | 2 |
| Barnyardgrass (Echinochloa crusgalli Beauv.) | 0 |
| Crabgrass (Digitaria sanguinalis Scop.) | 2 |
| Buckwheat (Polygonum convolvulus L.) | 3 |
| Morning Glory (mixture of Ipomoea purpurea Roth and Ipomoea hederacea Jacq.) | 2 |
| Untreated Controls | Normal |

EXAMPLE XXXVIII

Test Compound: 2',4'-Dinitro-6'-sec-butylphenyl 1H,1H,11H-eicosafluoroundecyl carbonate Observations made 13 days after application (left column)
Observations made 23 days after application (right column)

| Test Plant | Pre-Emergence | |
|---|---|---|
| | 10 lb./A | 10 lb./A |
| Yellow Nutsedge (Cyperus esculentus L.) | 0 | 0 |
| Wild Oats (Avena fatua L.) | 0 | 0 |
| Jimsonweed (Datura stramonium L.) | 8 | 8 |
| Velvetleaf (Abutilon theophrasti Medic.) | 6 | 4 |
| Johnsongrass (Sorghum halepense Pers.) | 0 | 0 |
| Pigweed (Amaranthus retroflexus L.) | 10 | 8 |
| Mustard (Brassica kaber L. C. Wheeler Var. pinnatifida L. C. Wheeler) | 10 | 10 |
| Yellow Foxtail (Setaria glauca Beauv.) | 9* | 9* |
| Barnyardgrass (Echinochloa crusgalli Beauv.) | 3 | 2 |
| Crabgrass (Digitaria sanguinalis Scop.) | 3 | 0 |
| Buckwheat (Polygonum convolvulus L.) | 3 | 0 |
| Morning Glory (mixture of Ipomoea purpurea Roth and Ipomoea hederacea Jacq.) | 2 | 1 |
| Untreated Controls | Normal | Normal |

*Possible bird damage

EXAMPLE XXXIX

Test Compound: 2',4'-Dinitro-6'-sec-butylphenyl 1H,1H,11H-eicosafluoroundecyl carbonate Observations made 12 days after application

| Test Plant | Post-Emergence 10 lb./A |
|---|---|
| Yellow Nutsedge (Cyperus esculentus L.) | 0 |
| Wild Oats (Avena fatua L.) | 0 |
| Jimsonweed (Datura stramonium L.) | 8 |
| Velvetleaf (Abutilon theophrasti Medic.) | 0 |
| Johnsongrass (Sorghum halepense Pers.) | 0 |
| Mustard (Brassica kaber L. C. Wheeler Var. pinnatifida L. C. Wheeler) | 0 |
| Yellow Foxtail (Setaria glauca Beauv.) | 0 |
| Barnyardgrass (Echinochloa crusgalli Beauv.) | 0 |
| Buckwheat (Polygonum convolvulus L.) | 9 |
| Morning Glory (mixture of Ipomoea purpurea Roth and Ipomoea hederacea Jacq.) | 0 |
| Red Kidney Bean (Phaseolus vulgaris L.) | 0 |
| Untreated Controls | Normal |

EXAMPLE XL

Test Compound: 2',4'-Dinitro-6'-sec-butylphenyl 1-(trifluoromethyl)-2,2,2-trifluoroethyl carbonate Observations made 13 days after application (left column)
Observations made 23 days after application (right column)

| Test Plant | Pre-Emergence 10 lb./A | 10 lb./A |
|---|---|---|
| Yellow Nutsedge (*Cyperus exculentus* L.) | 7 | 5 |
| Wild Oats (*Avena fatua* L.) | 4 | 5 |
| Jimsonweed (*Datura stramonium* L.) | 10 | 10 |
| Velvetleaf (*Abutilon theophrasti* Medic.) | 10 | 10 |
| Johnsongrass (*Sorghum halepense* Pers.) | 5 | 2 |
| Pigweed (*Amaranthus retroflexus* L.) | 10 | 10 |
| Mustard (*Brassica kaber* L. C. Wheeler Var. *pinnatifida* L. C. Wheeler) | 10 | 10 |
| Yellow Foxtail (*Setaria glauca* Beauv.) | 8* | 8* |
| Barnyardgrass (*Echinochloa crusgalli* Beauv.) | 6 | 4 |
| Crabgrass (*Digitaria sanguinalis* Scop.) | 6 | 5 |
| Buckwheat (*Polygonum convolvulus* L.) | 6 | 7 |
| Morning Glory (mixture of *Ipomoea purpurea* Roth and *Ipomoea hederacea* Jacq.) | 10 | 10 |
| Untreated Controls | Normal | Normal |

*Possible bird damage

EXAMPLE XLI

Test Compound: 2',4'-Dinitro-6'-sec-butylphenyl 1-(trifluoromethyl)-2,2,2-trifluoroethyl carbonate Observations made 12 days after application

| Test Plant | Post-Emergence 10 lb./A |
|---|---|
| Yellow Nutsedge (*Cyperus esculentus* L.) | 6 |
| Wild Oats (*Avena fatua* L.) | 6 |
| Jimsonweed (*Datura stramonium* L.) | 10 |
| Velvetleaf (*Abutilon theophrasti* Medic.) | 10 |
| Johnsongrass (*Sorghum halepense* Pers.) | 0 |
| Mustard (*Brassica kaber* L. C. Wheeler Var. *pinnatifida* L. C. Wheeler) | 10 |
| Yellow Foxtail (*Setaria glauca* Beauv.) | 2 |
| Barnyardgrass (*Echinochloa crusgalli* Beauv.) | 4 |
| Buckwheat (*Polygonum convolvulus* L.) | 10 |
| Morning Glory (mixture of *Ipomoea purpurea* Roth and *Ipomoea hederacea* Jacq.) | 6 |
| Red Kidney Bean (*Phaseolus vulgaris* L.) | 1 |
| Untreated Controls | Normal |

EXAMPLE XLII

Test Compound: 2',4'-Dinitrophenyl 2,2,3,3-tetrafluoropropyl carbonate

Observations made 13 days after application (left column)
Observations made 23 days after application (right column)

| Test Plant | Pre-Emergence 10 lb./A | 10 lb./A |
|---|---|---|
| Yellow Nutsedge (*Cyperus esculentus* L.) | 0 | 0 |
| Wild Oats (*Avena fatua* L.) | 0 | 0 |
| Jimsonweed (*Datura stramonium* L.) | 4 | 0 |
| Velvetleaf (*Abutilon theophrasti* Medic.) | 2 | 0 |
| Johnsongrass (*Sorghum halepense* Pers.) | 0 | 0 |
| Pigweed (*Amaranthus retroflexus* L.) | 5 | 0 |
| Mustard (*Brassica kaber* L. C. Wheeler Var. *pinnatifida* L. C. Wheeler) | 5 | 0 |
| Yellow Foxtail (*Setaria glauca* Beauv.) | 7* | 0 |
| Barnyardgrass (*Echinochloa crusgalli* Beauv.) | 0 | 0 |
| Crabgrass (*Digitaria sanguinalis* Scop.) | 0 | 0 |
| Buckwheat (*Polygonum convolvulus* L.) | 0 | 0 |
| Morning Glory (mixture of *Ipomoea purpurea* Roth and *Ipomoea hederacea* Jacq.) | 0 | 0 |
| Untreated Controls | Normal | Normal |

*Possible bird damage

EXAMPLE XLIII

Test Compound: 2',4'-Dinitrophenyl 2,2,3,3,-tetrafluoropropyl carbonate

Observations made 12 days after application

| Test Plant | Post-Emergence 10 lb./A |
|---|---|
| Yellow Nutsedge (*Cyperus esculentus* L.) | 0 |
| Wild Oats (*Avena fatua* L.) | 2 |
| Jimsonweed (*Datura stramonium* L.) | 10 |
| Velvetleaf (*Abutilon theophrasti* Medic.) | 3 |
| Johnsongrass (*Sorghum halepense* Pers.) | 0 |
| Mustard (*Brassica kaber* L. C. Wheeler Var. *pinnatifida* L. C. Wheeler) | 10 |
| Yellow Foxtail (*Setaria glauca* Beau.) | 0 |
| Barnyardgrass (*Echinochloa crusgalli* Beauv.) | 3 |
| Buckwheat (*Polygonum convolvulus* L.) | 10 |
| Morning Glory (mixture of *Ipomoea purpurea* Roth and *Ipomoea hederacea* Jacq.) | 3 |
| Red Kidney Bean (*Phaseolus vulgaris* L.) | 3 |
| Untreated Controls | Normal |

EXAMPLE XLIV

Test Compound: 2',6'-Dinitrophenyl 2,2,3,3-tetrafluoropropyl carbonate

Observations made 13 days after application (left column)
Observations made 23 days after application (right column)

| Test Plant | Pre-Emergence 10 lb./A | 10 lb./A |
|---|---|---|
| Yellow Nutsedge (*Cyperus esculentus* L.) | 0 | 0 |
| Wild Oats (*Avena fatua* L.) | 0 | 0 |
| Jimsonweed (*Datura stramonium* L.) | 0 | 0 |
| Velvetleaf (*Abutilon theophrasti* Medic.) | 0 | 0 |
| Johnsongrass (*Sorghum halepense* Pers.) | 0 | 0 |
| Pigweed (*Amaranthus retroflexus* L.) | 5 | 0 |
| Mustard (*Brassica kaber* L. C. Wheeler Var. *pinnatifida* L. C. Wheeler) | 5 | 0 |
| Yellow Foxtail (*Setaria glauca* Beauv.) | 0 | 0 |
| Barnyardgrass (*Echinochloa crusgalli* Beauv.) | 0 | 0 |
| Crabgrass (*Digitaria sanguinalis* Scop.) | 0 | 0 |
| Buckwheat (*Polygonum convolvulus* L.) | 0 | 0 |
| Morning Glory (mixture of *Ipomoea purpurea* Roth and *Ipomoea hederacea* Jacq.) | 0 | 0 |
| Untreated Controls | Normal | Normal |

EXAMPLE XLV

Test Compound: 2',6'-Dinitrophenyl 2,2,3,3-tetrafluoropropyl carbonate

Observations made 12 days after application

| Test Plant | Post-Emergence 10 lb./A |
|---|---|
| Yellow Nutsedge (*Cyperus esculentus* L.) | 0 |
| Wild Oats (*Avena fatua* L.) | 0 |
| Jimsonweed (*Datura stramonium* L.) | 10 |
| Velvetleaf (*Abutilon theophrasti* Medic.) | 3 |
| Johnsongrass (*Sorghum halepense* Pers.) | 0 |
| Mustard (*Brassica kaber* L. C. Wheeler Var. *pinnatifida* L. C. Wheeler) | 10 |
| Yellow Foxtail (*Setaria glauca* Beauv.) | 0 |
| Barnyardgrass (*Echinochloa crusgalli* Beauv.) | 0 |
| Buckwheat (*Polygonum convolvulus* L.) | 9 |
| Morning Glory (mixture of *Ipomoea purpurea* Roth and *Ipomoea hederacea* Jacq.) | 3 |
| Red Kidney Bean (*Phaseolus vulgaris* L.) | 0 |
| Untreated Controls | Normal |

EXAMPLE XLVI

Test Compound: 2',4'-Dinitro-6'-sec-butylphenyl 2-fluoroethyl carbonate

Observations made 13 days after application (left column)
Observations made 23 days after application (right column)

| Test Plant | Pre-Emergence 10 lb./A | 10 lb./A |
|---|---|---|
| Yellow Nutsedge (*Cyperus esculentus* L.) | 0 | 0 |
| Wild Oats (*Avena fatua* L.) | 3 | 4 |
| Jimsonweed (*Datura stramonium* L.) | 10 | 10 |
| Velvetleaf (*Abutilon theophrasti* Medic.) | 8 | 7 |
| Johnsongrass (*Sorghum halepense* Pers.) | 4 | 2 |
| Pigweed (*Amaranthus retroflexus* L.) | 10 | 10 |
| Mustard (*Brassica kaber* L. C. Wheeler Var. *pinnatifida* L. C. Wheeler) | 10 | 10 |
| Yellow Foxtail (*Setaria glauca* Beauv.) | 8* | 8* |
| Barnyardgrass (*Echinochloa crusgalli* Beauv.) | 9 | 8 |
| Crabgrass (*Digitaria sanguinalis* Scop.) | 6 | 5 |
| Buckwheat (*Polygonum convolvulus* L.) | 7 | 9 |
| Morning Glory (mixture of *Ipomoea purpurea* Roth and *Ipomoea hederacea* Jacq.) | 10 | 10 |
| Untreated Controls | Normal | Normal |

*Possible bird damage

EXAMPLE XLVII

Test Compound: 2',4'-Dinitro-6'-sec-butylphenyl 2-fluoroethyl carbonate

Observations made 12 days after application

| Test Plant | Post-Emergence 10 lb./A |
|---|---|
| Yellow Nutsedge (*Cyperus esculentus* L.) | 0 |
| Wild Oats (*Avena fatua* L.) | 3 |
| Jimsonweed (*Datura stramonium* L.) | 10 |
| Velvetleaf (*Abutilon theophrasti* Medic.) | 4 |
| Johnsongrass (*Sorghum halepense* Pers.) | 0 |
| Mustard (*Brassica kaber* L. C. Wheeler Var. *pinnatifida* L. C. Wheeler) | 10 |
| Yellow Foxtail (*Setaria glauca* Beauv.) | 0 |
| Barnyardgrass (*Echinochloa crusgalli* Beauv.) | 3 |
| Buckwheat (*Polygonum convolvulus* L.) | 10 |
| Morning Glory (mixture of *Ipomoea purpurea* Roth and *Ipomoea hederacea* Jacq.) | 4 |
| Red Kidney Bean (*Phaseolus vulgaris* L.) | 0 |
| Untreated Controls | Normal |

EXAMPLE XLVIII

Test Compound: 2',4'-Dinitro-6'-tert-butylphenyl 2,2,3,3-tetrafluoropropyl carbonate Observations made 13 days after application (left column)
Observations made 23 days after application (right column)

| Test Plant | Pre-Emergence 10 lb./A | 10 lb./A |
|---|---|---|
| Yellow Nutsedge (*Cyperus esculentus* L.) | 0 | 0 |
| Wild Oats (*Avena fatua* L.) | 3 | 3 |
| Jimsonweed (*Datura stramonium* L.) | 10 | 10 |
| Velvetleaf (*Abutilon theophrasti* Medic.) | 9 | 8 |
| Johnsongrass (*Sorghum halepense* Pers.) | 2 | 0 |
| Pigweed (*Amaranthus retroflexus* L.) | 10 | 10 |
| Mustard (*Brassica kaber* L. C. Wheeler Var. *pinnatifida* L. C. Wheeler) | 10 | 10 |
| Yellow Foxtail (*Setaria glauca* Beauv.) | 6* | 6* |
| Barnyardgrass (*Echinochloa crusgalli* Beauv.) | 7 | 4 |
| Crabgrass (*Digitaria sanguinalis* Scop.) | 6 | 3 |
| Buckwheat (*Polygonum convolvulus* L.) | 7 | 10 |
| Morning Glory (mixture of *Ipomoea purpurea* Roth and *Ipomoea hederacea* Jacq.) | 9 | 10 |
| Untreated Controls | Normal | Normal |

*Possible bird damage

EXAMPLE XLIX

Test Compound: 2',4'-Dinitro-6'-tert-butylphenyl 2,2,3,3-tetrafluoropropyl carbonate Observations made 12 days after application

| Test Plant | Post-Emergence 10 lb./A |
|---|---|
| Yellow Nutsedge (*Cyperus esculentus* L.) | 0 |
| Wild Oats (*Avena fatua* L.) | 0 |
| Jimsonweed (*Datura stramonium* L.) | 10 |
| Velvetleaf (*Abutilon theophrasti* Medic.) | 5 |
| Johnsongrass (*Sorghum halepense* Pers.) | 1 |
| Mustard (*Brassica kaber* L. C. Wheeler Var. *pinnatifida* L. C. Wheeler) | 10 |
| Yellow Foxtail (*Setaria glauca* Beauv.) | 0 |
| Barnyardgrass (*Echinochloa crusgalli* Beauv.) | 0 |
| Buckwheat (*Polygonum convolvulus* L.) | 10 |
| Morning Glory (mixture of *Ipomoea purpurea* Roth and *Ipomoea hederacea* Jacq.) | 0 |
| Red Kidney Bean (*Phaseolus vulgaris* L.) | 0 |
| Untreated Controls | Normal |

EXAMPLE L

Test Compound: 2',4'-Dinitro-6'-sec-butylphenyl 1H,1H,7H-dodecafluoroheptyl carbonate Observations made 13 days after application (left column)
Observations made 23 days after application (right column)

| Test Plant | Pre-Emergence 10 lb./A | 10 lb./A |
|---|---|---|
| Yellow Nutsedge (*Cyperus esculentus* L.) | 0 | 0 |
| Wild Oats (*Avena fatua* L.) | 0 | 0 |
| Jimsonweed (*Datura stramonium* L.) | 2 | 0 |
| Velvetleaf (*Abutilon theophrasti* Medic.) | 7 | 0 |
| Johnsongrass (*Sorghum halepense* Pers.) | 0 | 0 |
| Pigweed (*Amaranthus retroflexus* L.) | 3 | 0 |
| Mustard (*Brassica kaber* L. C. Wheeler Var. *pinnatifida* L. C. Wheeler) | 1 | 0 |
| Yellow Foxtail (*Setaria glauca* Beauv.) | 0 | 0 |
| Barnyardgrass (*Chinochloa crusgalli* Beauv.) | 0 | 0 |
| Crabgrass (*Digitaria sanguinalis* Scop.) | 0 | 0 |
| Buckwheat (*Polygonum convolvulus* L.) | 0 | 0 |
| Morning Glory (mixture of *Ipomoea purpurea* Roth and *Ipomoea hederacea* Jacq.) | 0 | 0 |
| Untreated Controls | Normal | Normal |

EXAMPLE LI

Test Compound: 2',4'-Dinitro-6'-sec-butylphenyl 1H,1H,7H-dodecafluoroheptyl carbonate Observations made 12 days after application

| Test Plant | Post-Emergence 10 lb./A |
|---|---|
| Yellow Nutsedge (*Cyperus esculentus* L.) | 0 |
| Wild Oats (*Avena fatua* L.) | 1 |
| Jimsonweed (*Datura stramonium* L.) | 1 |
| Velvetleaf (*Abutilon theophrasti* Medic.) | 1 |
| Johnsongrass (*Sorghum halepense* Pers.) | 0 |
| Mustard (*Brassica kaber* L. C. Wheeler Var. *pinnatifida* L. C. Wheeler) | 1 |
| Yellow Foxtail (*Setaria glauca* Beauv.) | 1 |
| Barnyardgrass (*Echinochloa crusgalli* Beauv.) | 1 |
| Buckwheat (*Polygonum convolvulus* L.) | 0 |
| Morning Glory (mixture of *Ipomoea purpurea* Roth and *Ipomoea hederacea* Jacq.) | 2 |
| Red Kidney Bean (*Phaseolus vulgaris* L.) | 1 |
| Untreated Controls | Normal |

EXAMPLE LI(a)

Test Compound: 2',4'-Dinitro-6'-cyclohexylphenyl 2-fluoroethyl carbonate

Pre-Emergence Observations made 13 days after application
Post-Emergence Observations made 13 days after application

| Test Plant | Pre-Emergence 10 lb./A | Post-Emergence 10 lb./A |
|---|---|---|
| Yellow Nutsedge (*Cyperus esculentus* L.) | 0 | 0 |
| Wild Oats (*Avena fatua* L.) | 3 | 0 |
| Jimsonweed (*Datura stramonium* L.) | 5 | 10 |
| Velvetleaf (*Abutilon theophrasti* Medic.) | 3 | 0 |
| Johnsongrass (*Sorghum halepense* Pers.) | 1 | 0 |
| Pigweed (*Amaranthus retroflexus* L.) | 4 | — |
| Mustard (*Brassica kaber* L. C. Wheeler Var. *pinnatifida* L. C. Wheeler) | 9 | 5 |
| Yellow Foxtail (*Setaria glauca* Beauv.) | 0 | 0 |
| Barnyardgrass (*Echinochloa crusgalli* Beauv.) | 0 | 0 |
| Crabgrass (*Digitaria sanguinalis* Scop.) | 4 | — |
| Buckwheat (*Polygonum convolvulus* L.) | 2 | 6 |
| Morning Glory (mixture of *Ipomoea purpurea* Roth and *Ipomoea hederacea* Jacq.) | 1 | 1 |
| Canada Thistle (*Cirsium arvense* [L.] Scop.) | — | 9 |
| Cotton (*Gossypium hirsutum* L.) | — | 0 |
| Untreated Controls | Normal | Normal |

EXAMPLE LI(b)

Test Compound: 2',4'-Dinitro-6'-cyclohexylphenyl 1-(trifluoromethyl)-2,2,2-trifluoroethyl carbonate Pre-Emergence Observations made 13 days after application
Post-Emergence Observations made 13 days after application

| Test Plant | Pre-Emergence 10 lb./A | Post-Emergence 10 lb./A |
|---|---|---|
| Yellow Nutsedge (*Cyperus esculentus* L.) | 0 | 0 |
| Wild Oats (*Avena fatua* L.) | 3 | 6 |
| Jimsonweed (*Datura stramonium* L.) | 5 | 10 |
| Velvetleaf (*Abutilon theophrasti* Medic.) | 2 | 10 |
| Johnsongrass (*Sorghum halepense* Pers.) | 1 | 1 |
| Pigweed (*Amaranthus retroflexus* L.) | 5 | — |
| Mustard (*Brassica kaber* L. C. Wheeler Var. *pinnatifida* L. C. Wheeler) | 9 | 9 |
| Yellow Foxtail (*Setaria glauca* Beauv.) | 1 | 3 |
| Barnyardgrass (*Echinochloa crusgalli* Beauv.) | 0 | 3 |
| Crabgrass (*Digitaria sanguinalis* Scop.) | 7 | — |
| Buckwheat (*Polygonum convolvulus* L.) | 5 | 10 |
| Morning Glory (mixture of *Ipomoea purpurea* Roth and *Ipomoea hederacea* Jacq.) | 2 | 3 |
| Canada Thistle (*Cirsium arvense* [L.] Scop.) | — | 9 |
| Cotton (*Gossypium hirsutum* L.) | — | 0 |
| Untreated Controls | Normal | Normal |

EXAMPLE LI(c)

Test Compound: 2',4'-Dinitro-6'-cyclohexylphenyl 1-(trifluoromethyl)-2,2,2-trifluoroethyl carbonate Observations made 19 days after application

| Test Plant | Pre-Emergence 10 lb./A |
|---|---|
| Yellow Nutsedge (*Cyperus esculentus* L.) | 0 |
| Wild Oats (*Avena fatua* L.) | 2 |
| Jimsonweed (*Datura stramonium* L.) | 0 |
| Velvetleaf (*Abutilon theophrasti* Medic.) | 0 |
| Johnsongrass (*Sorghum halepense* Pers.) | 0 |
| Pigweed (*Amaranthus retroflexus* L.) | 0 |
| Mustard (*Brassica kaber* L. C. Wheeler Var. *pinnatifida* L. C. Wheeler) | 10 |
| Yellow Foxtail (*Setaria glauca* Beauv.) | 0 |
| Barnyardgrass (*Echinochloa crusgalli* Beauv.) | 0 |
| Crabgrass (*Digitaria sanguinalis* Scop.) | 5 |
| Buckwheat (*Polygonum convolvulus* L.) | 5 |
| Morning Glory (mixture of *Ipomoea purpurea* Roth and *Ipomoea hederacea* Jacq.) | 0 |
| Untreated Controls | Normal |

EXAMPLE LI(d)

Test Compound: 2',4'-Dinitro-6'-cyclohexylphenyl 1H,1H,7H-dodecafluoroheptyl carbonate Pre-Emergence Observations made 13 days after application
Post-Emergence Observations made 13 days after application

| Test Plant | Pre-Emergence 10 lb./A | Post-Emergence 10 lb./A |
|---|---|---|
| Yellow Nutsedge (*Cyperus esculentus* L.) | 0 | 0 |
| Wild Oats (*Avena fatua* L.) | 2 | 0 |
| Jimsonweed (*Datura stramonium* L.) | 6 | 10 |
| Velvetleaf (*Abutilon theophrasti* Medic.) | 0 | 0 |
| Johnsongrass (*Sorghum halepense* Pers.) | 0 | 0 |
| Pigweed (*Amaranthus retroflexus* L.) | 5 | — |
| Mustard (*Brassica kaber* L. C. Wheeler Var. *pinnatifida* L. C. Wheeler) | 10 | 10 |
| Yellow Foxtail (*Setaria glauca* Beauv.) | 0 | 0 |
| Barnyardgrass (*Echinochloa crusgalli* Beauv.) | 0 | 0 |
| Crabgrass (*Digitaria sanguinalis* Scop.) | 6 | — |
| Buckwheat (*Polygonum convolvulus* L.) | 2 | 3 |
| Morning Glory (mixture of *Ipomoea purpurea* Roth and *Ipomoea hederacea* Jacq.) | 0 | 0 |
| Canada Thistle (*Cirsium arvense* [L.] Scop.) | — | 2 |
| Cotton (*Gossypium hirsutum* L.) | — | 0 |
| Untreated Controls | Normal | Normal |

EXAMPLE LI(e)

Test Compound: 2',4'-Dinitro-6'-cyclohexylphenyl 1H,1H,7H-dodecafluoroheptyl carbonate Observations made 19 days after application

| Test Plant | Pre-Emergence 10 lb./A |
|---|---|
| Yellow Nutsedge (*Cyperus esculentus* L.) | 0 |
| Wild Oats (*Avena fatua* L.) | 0 |
| Jimsonweed (*Datura stramonium* L.) | 6 |
| Velvetleaf (*Abutilon theophrasti* Medic.) | 2 |
| Johnsongrass (*Sorghum halepense* Pers.) | 0 |

EXAMPLE LI(e)-continued

Test Compound: 2',4'-Dinitro-6'-cyclohexylphenyl 1H,1H,7H-dodecafluoroheptyl carbonate Observations made 19 days after application

| Test Plant | Pre-Emergence 10 lb./A |
|---|---|
| Pigweed (Amaranthus retroflexus L.) | 0 |
| Mustard (Brassica kaber L. C. Wheeler Var. pinnatifida L. C. Wheeler) | 10 |
| Yellow Foxtail (Setaria glauca Beauv.) | 0 |
| Barnyardgrass (Echinochloa crusgalli Beauv.) | 0 |
| Crabgrass (Digitaria sanguinalis Scop.) | 4 |
| Buckwheat (Polygonum convolvulus L.) | 0 |
| Morning Glory (mixture of Ipomoea purpurea Roth and Ipomoea hederacea Jacq.) | 0 |
| Untreated controls | Normal |

EXAMPLE LI(f)

Test Compound: 2',4'-Dinitro-6'-cyclohexylphenyl 1H,1H,11H-eicosafluoroundecyl carbonate Pre-Emergence Observations made 13 days after application
Post-Emergence Observations made 13 days after application

| Test Plant | Pre-Emergence 10 lb./A | Post-Emergence 10 lb./A |
|---|---|---|
| Yellow Nutsedge (Cyperus esculentus L.) | 0 | 0 |
| Wild Oats (Avena fatua L.) | 0 | 0 |
| Jimsonweed (Datura stramonium L.) | 0 | 0 |
| Velvetleaf (Abutilon theophrasti Medic.) | 0 | 0 |
| Johnsongrass (Sorghum halepense Pers.) | 0 | 0 |
| Pigweed (Amaranthus retroflexus L.) | 5 | — |
| Mustard (Brassica kaber L. C. Wheeler Var. pinnatifida L. C. Wheeler) | 10 | 0 |
| Yellow Foxtail (Setaria glauca Beauv.) | 0 | 0 |
| Barnyardgrass (Echinochloa crusgalli Beauv.) | 0 | 0 |
| Crabgrass (Digitaria sanguinalis Scop.) | 3 | — |
| Buckwheat (Polygonum convolvulus L.) | 2 | 0 |
| Morning Glory (mixture of Ipomoea purpurea Roth and Ipomoea hederacea Jacq.) | 0 | 0 |
| Canada Thistle (Cirsium arvense [L.] Scop.) | — | 0 |
| Cotton (Gossypium hirsutum L.) | — | 0 |
| Untreated Controls | Normal | Normal |

Many of the carbonates of this invention possess properties which make them useful as fungicides. Fungi may be killed by bringing a fungicidal amount of the carbonate and the fungi into mutual contact, as for example, by applying the carbonate directly to the fungi. In another embodiment the carbonate is applied to a region where fungi are likely to be found in order to preclude fungi from becoming established.

The formulations used as fungicides are similar in all material respects to those described above for miticidal purposes. The concentration of the carbonate compound in the formulation and the total amount applied will vary depending upon the particular carbonate being employed and the particular fungus being confronted. Other factors such as season of the year, environmental conditions, and stage of fungi development all have their effect. Exemplary concentrations employed range from about 1 to about 5000 parts per million by weight (ppm). Usually the concentration will range from about 10 to about 1000 ppm. Concentrations of from about 10 to about 250 ppm are most often used. Liquid formulations having such concentrations are ordinarily applied until the area of application is well wetted. Dusts of formulations having these concentrations are typically applied until a light coating of powder appears on the area being treated.

EXAMPLE LII

Test compounds are formulated for fungicidal testing in the same manner as described in Example XVI. Cheyenne wheat plants (Triticum fulgare), approximately 7 to 8 days old and 4 to 5 inches tall are mounted on a compound turntable and sprayed with the test formulations at the concentrations indicated. The wheat plants are thoroughly wetted with the test formulation. After drying, the treated wheat plants are dusted with spores of leaf rust of wheat (Puccinia rubigo-vera) directly from diseased plants and then immediately placed in an incubation chamber maintained at 70° F. and a relative humidity greater than 95 percent. After an overnight incubation period, the test plants are removed to the greenhouse where they are held for a period of 3 to 5 days for disease development. Control plants are similarly processed except that they are not treated with test compound. After the disease development period, the pustules developed on both the inoculated but otherwise untreated control plants and the innoculated and treated plants are counted. Data is reported as Percent Control which is computed in accordance with the following formula:

$$\text{Per Cent Control} = \left(1.0 - \frac{\text{avg. no. pustules on treated plants}}{\text{avg. no. pustules on untreated plants}}\right) \times 100$$

Table 26 reports observed results where the test compound is 2',4'-dinitro-6'-cyclohexylphenyl 2,2,3,3-tetrafluoropropyl carbonate.

Table 26

Fungicidal Effectiveness of 2',4'-Dinitro-6'-cyclohexylphenyl 2,2,3,3-Tetrafluoropropyl Carbonate as Protectant Against Leaf Rust of Wheat (Puccinia rubigo-vera)

| Concentration ppm | Per Cent Control |
|---|---|
| 1,000 | 100 |
| 250 | 100 |
| 100 | 100 |

Table 26-continued

Fungicidal Effectiveness of 2',4'-Dinitro-6'-cyclohexylphenyl 2,2,3,3-Tetrafluoropropyl Carbonate as Protectant Against Leaf Rust of Wheat (Puccinia rubigo-vera)

| Concentration ppm | Per Cent Control |
|---|---|
| 50 | 99, 100 |
| 25 | 81 |
| 10 | 30 |

EXAMPLE LIII

The procedure of Example LII is followed except that the test compound is 2',4'-dinitro-6'-sec-butylphenyl 2,2,3,3-tetrafluoropropyl carbonate. Table 27 reports the observed results of this test.

Table 27

Fungicidal Effectiveness of 2',4'-Dinitro-6'-sec-butylphenyl 2,2,3,3-Tetrafluoropropyl Carbonate as Protectant Against Leaf Rust of Wheat (Puccinia rubigo-vera)

| Concentration ppm | Per Cent Control |
|---|---|
| 1,000 | 100 |
| 100 | 95 |
| 50 | 100 |
| 25 | 92 |
| 10 | 69 |

EXAMPLE LIV

The procedure of Example LII is followed except that the test compound is 2',4'-dinitro-6'-methylphenyl 2,2,3,3-tetrafluoropropyl carbonate. Table 28 reports the observed results of the test.

Table 28

Fungicidal Effectiveness of 2',4'-Dinitro-6'-methylphenyl 2,2,3,3-Tetrafluoropropyl Carbonate as Protectant Against Leaf Rust of Wheat (Puccinia rubigo-vera)

| Concentration ppm | Per Cent Control |
|---|---|
| 1,000 | 100 |
| 250 | 100 |
| 100 | 100 |
| 50 | 45 |

EXAMPLE LV

The procedure of Example LII is followed except that the test compound is 2',4'-dinitro-6'-sec-butylphenyl 2,2,2-trifluoroethyl carbonate. Table 29 reports the observed results of the test.

Table 29

Fungicidal Effectiveness of 2',4'-Dinitro-6'-sec-butylphenyl 2,2,2-Trifluoroethyl Carbonate as Protectant Against Leaf Rust of Wheat (Puccinia rubigo-vera)

| Concentration ppm | Per Cent Control |
|---|---|
| 1,000 | 100 |
| 250 | 99 |
| 100 | 69 |

EXAMPLE LVI

The procedure of Example LII is followed except that the test compound is 2',4'-dinitro-6'-sec-butylphenyl 1H,1H,11H-eicosafluoroundecyl carbonate. Table 30 reports the observed results.

Table 30

Fungicidal Effectiveness of 2',4'-Dinitro-6'-sec-butylphenyl 1H,1H,11H-eicosafluoroundecyl Carbonate as Protectant Against Leaf Rust of Wheat (Puccinia rubigo-vera)

| Concentration ppm | Per Cent Control |
|---|---|
| 1,000 | 64 |

EXAMPLE LVII

The procedure of Example LII is followed except that the test compound is 2',4'-dinitro-6'-sec-butylphenyl 1-(trifluoromethyl)-2,2,2-trifluoroethyl carbonate. Table 31 reports the observed results.

Table 31

Fungicidal Effectiveness of 2',4'-Dinitro-6'-sec-butylphenyl 1-(trifluoromethyl)-2,2,2-trifluoroethyl Carbonate as Protectant Against Leaf Rust of Wheat (Puccinia rubigo-vera)

| Concentration ppm | Per Cent Control |
|---|---|
| 1,000 | 100 |

EXAMPLE LVIII

The procedure of Example LII is followed except that the test compound is 2',4'-dinitrophenyl 2,2,3,3-tetrafluoropropyl carbonate. Table 32 reports the observed results.

Table 32

Fungicidal Effectiveness of 2',4'-Dinitrophenyl 2,2,3,3-Tetrafluoropropyl Carbonate as Protectant Against Leaf Rust of Wheat (Puccinia rubigo-vera)

| Concentration ppm | Per Cent Control |
|---|---|
| 1,000 | 100 |

EXAMPLE LIX

The procedure of Example LII is followed except that the test compound is 2',6'-dinitrophenyl 2,2,3,3-tetrafluoropropyl carbonte. Table 33 reports the observed results.

Table 33

Fungicidal Effectiveness of 2',6'-Dinitrophenyl 2,2,3,3-Tetrafluoropropyl Carbonate as Protectant Against Leaf Rust of Wheat (Puccinia rubigo-vera)

| Concentration ppm | Per Cent Control |
|---|---|
| 1,000 | 100 |

EXAMPLE LX

The procedure of Example LII is followed except that the test compound is 2',4'-dinitro-6'-sec-butylphenyl 2-fluoroethyl carbonate. Table 34 reports the observed results.

Table 34

Fungicidal Effectiveness of 2',4'-Dinitro-6'-
sec-butylphenyl 2-Fluoroethyl Carbonate
as Protectant Against
Leaf Rust of Wheat (*Puccinia rubigo-vera*)

| Concentration ppm | Per Cent Control |
|---|---|
| 1,000 | 100 |

EXAMPLE LXI

The procedure of Example LII is followed except that the test compound is 2',4'-dinitro-6'-tert-butylphenyl 2,2,3,3-tetrafluoropropyl carbonate. Table 35 reports the observed results.

Table 35

Fungicidal Effectiveness of 2',4'-Dinitro-6'-
tert-butylphenyl 2,2,3,3-Tetrafluoropropyl Carbonate
as Protectant Against
Leaf Rust of Wheat (*Puccinia rubigo-vera*)

| Concentration ppm | Per Cent Control |
|---|---|
| 1,000 | 81 |

EXAMPLE LXII

The procedure of Example LII is followed except that the test compound is 2',4'-dinitro-6'-sec-butylphenyl 1H,1H,7H-dodecafluoroheptyl carbonate. Table 36 reports the observed results:

Table 36

Fungicidal Effectiveness of 2',4'-Dinitro-6'-
sec-butylphenyl 1H,1H,7H-Dodecafluoroheptyl
Carbonate as Protectant Against
Leaf Rust of Wheat (*Puccinia rubigo-vera*)

| Concentration ppm | Per Cent Control |
|---|---|
| 1,000 | 100 |

While the invention has been described with reference to certain illustrative embodiments, it is not intended that it shall be limited thereby except insofar as appears in the accompanying claims.

We claim:

1. A method of killing weeds which comprises applying to the soil in the vicinity of the weeds a phytocidal amount of a compound represented by the structural formula:

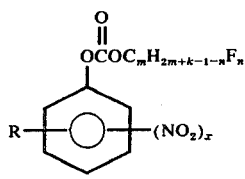

wherein
 $x$ is 1, 2 or 3;
 $k$ is −2, 0 or 2;
 $m$ is an integer ranging from 1 to 15 when $k$ is 2;
 $m$ is an integer ranging from 2 to 15 when $k$ is 0 or −2;
 $n$ is an integer ranging from 1 to $(2m+k-1)$; and
 R is hydrogen, lower alkyl, halo lower alkyl, lower alkenyl, halo lower alkenyl, lower alkylthio, halo lower alkylthio, lower alkenylthio, halo lower alkenylthio, lower cycloalkyl or halo lower cycloalkyl.

2. The method of claim 1 wherein the value of $k$ is 2 and R is selected from the group consisting of lower alkyl containing from 1 to 8 carbon atoms and lower cycloalkyl containing from 3 to 8 carbon atoms.

3. The method of claim 2 wherein:
 a. the value of $x$ is 2;
 b. the nitro groups are located in the 2',4'-positions; and
 c. R is located in the 6'-position.

4. The method of claim 3 wherein R is secondary butyl or cyclohexyl.

5. The method of claim 3 wherein the compound is 2',4'-dinitro-6'-sec-butylphenyl 2,2,3,3-tetrafluoropropyl carbonate.

6. A method of killing weeds which comprises bringing into mutual contact the weeds and a phytocidal amount of a compound represented by the structural formula:

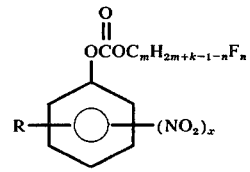

wherein
 $x$ is 1, 2 or 3;
 $k$ is −2, 0 or 2;
 $m$ is an integer ranging from 1 to 15 when $k$ is 2;
 $m$ is an integer ranging from 2 to 15 when $k$ is 0 or 2;
 $n$ is an integer ranging from 1 to $(2m+k-1)$; and
 R is hydrogen, lower alkyl, halo lower alkyl, lower alkenyl, halo lower alkenyl, lower alkylthio, halo lower alkylthio, lower alkenylthio, halo lower alkenylthio, lower cycloalkyl or halo lower cycloalkyl.

7. The method of claim 6 wherein the value of $k$ is 2 and R is selected from the group consisting of lower alkyl containing from 1 to 8 carbon atoms and lower cycloalkyl containing from 3 to 8 carbon atoms.

8. The method of claim 7 wherein:
 a. the value of $x$ is 2;
 b. the nitro groups are located in the 2',4'-positions; and
 c. R is located in the 6'-position.

9. The method of claim 8 wherein R is secondary butyl or cyclohexyl.

10. The method of claim 9 wherein the compound is 2',4'-dinitro-6'-sec-butylphenyl 2,2,3,3-tetrafluoropropyl carbonate.

11. A method of precluding the establishment of a weed population in the soil comprising applying to the soil an effective amount of a compound represented by the structural formula:

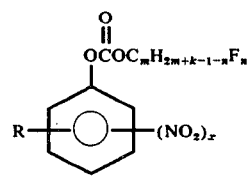

wherein
 $x$ is 1, 2 or 3;

$k$ is −2, 0 or 2;

$m$ is an integer ranging from 1 to 15 when $k$ is 2;

$m$ is an integer ranging from 2 to 15 when $k$ is 0 or −2;

$n$ is an integer ranging from 1 to ($2m+k-1$); and

R is hydrogen, lower alkyl, halo lower alkyl, lower alkenyl, halo lower alkenyl, lower alkylthio, halo lower alkylthio, lower alkenylthio, halo lower alkenylthio, lower cycloalkyl or halo lower cycloalkyl.

12. The method of claim 11 wherein the value of $k$ is 2 and R is selected from the group consisting of lower alkyl containing from 1 to 8 carbon atoms and lower cycloalkyl containing from 3 to 8 carbon atoms.

13. The method of claim 12 wherein:
  a. the value of $x$ is 2;
  b. the nitro groups are located in the 2',4'-positions; and
  c. R is located in the 6'-position.

14. The method of claim 13 wherein R is secondary butyl or cyclohexyl.

15. The method of claim 14 wherein the compound is 2',4'-dinitro-6'-sec-butylphenyl 2,2,3,3-tetrafluoropropyl carbonate.

* * * * *

UNITED STATES PATENT AND TRADEMARK OFFICE
CERTIFICATE OF CORRECTION

PATENT NO. : 4,022,609

DATED : May 10, 1977

INVENTOR(S) : Donald E. Hardies and Jay K. Rinehart

It is certified that error appears in the above-identified patent and that said Letters Patent are hereby corrected as shown below:

Column 46, line 34, "2" should be --- -2 ---.

Signed and Sealed this second Day of August 1977

[SEAL]

Attest:

RUTH C. MASON
*Attesting Officer*

C. MARSHALL DANN
*Commissioner of Patents and Trademarks*